(12) United States Patent
Hartwich et al.

(10) Patent No.: US 7,601,848 B2
(45) Date of Patent: Oct. 13, 2009

(54) MULTIFUNCTIONAL REAGENT FOR THE SYNTHESIS OF THIOL MODIFIED OLIGOMERS

(75) Inventors: Gerhard Hartwich, München (DE); Peter Frischmann, München (DE); Elisenda Ferrer, München (DE)

(73) Assignee: Fidicula GmbH, Munich (DE)

( * ) Notice: Subject to any disclaimer, the term of this patent is extended or adjusted under 35 U.S.C. 154(b) by 634 days.

(21) Appl. No.: 10/499,887

(22) PCT Filed: Dec. 21, 2002

(86) PCT No.: PCT/DE02/04699

§ 371 (c)(1),
(2), (4) Date: Mar. 1, 2005

(87) PCT Pub. No.: WO03/055852

PCT Pub. Date: Jul. 10, 2003

(65) Prior Publication Data
US 2005/0153291 A1 Jul. 14, 2005

(30) Foreign Application Priority Data
Dec. 22, 2001 (DE) .............................. 101 63 836

(51) Int. Cl.
*C07D 339/04* (2006.01)
(52) U.S. Cl. .......................................... 549/20; 549/22
(58) Field of Classification Search ................... 549/20, 549/22
See application file for complete search history.

(56) References Cited

U.S. PATENT DOCUMENTS 6,321,906 B1   11/2001   Wein

FOREIGN PATENT DOCUMENTS

| EP | 0523 978 | 1/1993 |
|----|----------|--------|
| JP | 2000-204087 | 7/2000 |
| WO | WO 98/01440 A2 | 1/1998 |
| WO | WO 00/42217 | 7/2000 |

OTHER PUBLICATIONS

Luettrinhaus et al., Cyclic Disulfides. IV. Proton Resonance Investigation of Constellation Mobility In the Substituted 1,2-dithiane Ring, Zeitschrift Fuer Naturforschung; (1961), 16b; 761-762.*
Parham, M.E. et al., "Carboxyl-Terminal Sequential Degradation" *Biochem. Biophys. Res. Commun.*, vol. 1, pp. 1-6, 1978.
Lund, V. et al, "Assessment of Methods for Covalent Binding of Nucleic Acids to Magnetic Beads, Dynabeads™, and the Characteristics of the Bound Nucleic Acids in Hybridization Reactions" *Nucl. Acids Res.* vol. 16: pp. 10861-10880, 1988.
Nuzzo, R.G., et al., "Adsorption of Bifunctional Organic Disulfides on Gold Surfaces" *J. Am. Chem.* Soc. vol. 105, pp. 4481-4483, 1983.

Bain, C.D. et al., "Formation of Monolayer Films by the Spontaneous Assembly of Organic Thiols from Solution onto Gold" *J. Am. Chem. Soc.* vol. 111, pp. 321-335, 1989.
Bain, C.D. et al., "Formation of Monolayers by the Coadsorption of Thiols on Gold: Variation in the Head Group, Tail Group, and Solvent" *J. Am. Chem. Soc.* vol. 111, pp. 7155-7164, 1989.
Lee, T.R. et al., Heterogeneous Catalysis on Platinum and Self-assembled Monolayers on Metal and Metal Oxide Surfaces (Note a) *Pure & Appl. Chem.* vol. 63, pp. 821-828, 1991.
Nuzzo, R.G. et al. "Absorption of Bifunctional Organic Disulfides on Gold Surfaces" *J. Am. Chem. Soc.*, vol. 105, pp. 4481-4483, 1983.
Letsinger, R.L. "Use of a Steroid Cyclic Disulfide Anchor in Constructing Gold Nanoparticle-Oligonucleotide Conjugates" Bioconjuqate Chemistry vol. 11, pp. 289-291, 2000.

(Continued)

*Primary Examiner*—James O Wilson
*Assistant Examiner*—Ebenezer Sackey
(74) *Attorney, Agent, or Firm*—K. David Crockett, Esq.; Crockett & Crockett

(57) ABSTRACT

The invention relates to compounds of formula (I), wherein Z represents a hydrocarbon with 2 to 28 C atoms, wherein Z can also comprise elements N, O, P, S, Si and halogen as heteroatoms, $R^1$ and $R^2$ are identical or different sulfur protecting groups, wherein both S atoms can also form a disulfide bridge and in said case $R^1$ and $R^2$ are not present; protecting group $Y^1$ represents protecting group NH, protecting group $NR^4$, protecting group O, CONH protecting group, protecting group OOC, protecting group S—S, —CH(protecting group O)$_2$ or —$CR^5$(protecting group O)$_2$ or protecting group S; $Y^2$ represents —OH, —$NH_2$, —$NHR^3$, —$NR^3R^4$, —COOH, —COCl, —COOCO—$R^6$, —$CONH_2$, —$CONHR^3$, —$COOR^3$, —$SO_3H$, —$SO_3$cI, —SH, —S—$SR^3$, —CHO, —$COR^3$, —$C_2H_3O$, halogen, —$N_3$, —NH—$NH_2$, —NCO, —NCS, wherein $R^3$ represents alkyl, heteroalkyl, aryl, cycloalkyl or a protecting group, wherein $R^3$ can be identical or different in groups $Y^1$ and $Y^2$, $R^4$ is s protecting group, wherein $R^4$ can be identical or different in groups $Y^1$ and $Y^2$, and wherein $R^4$ and $R^3$ can be identical or different, $R^5$ represents alkyl, aryl or cycloalkyl, wherein $R^5$ can be identical or different in groups $Y^1$ and $Y^2$ and $R^6$ represents alkyl, heteroalkyl, aryl or cycloalkyl, wherein $R^6$ can be identical or different in groups $Y^1$ and $Y^2$, wherein $Y^2$ can also represent a group of formula (II) or formula (III), wherein $X^1$ represents halogen or a substituted amine, $X^2$ represents an alkyl, alkoxy, aryloxy radical or a cyano derivative of an alkyl, alkoxy, aryloxy radical, $X^3$ represents halogen, an amino function or oxygen and $X^4$ represents an alkyl, alkoxy, aryloxy radical or $X^4$ equals H if $X^3$=oxygen.

(I)

Figure 1:
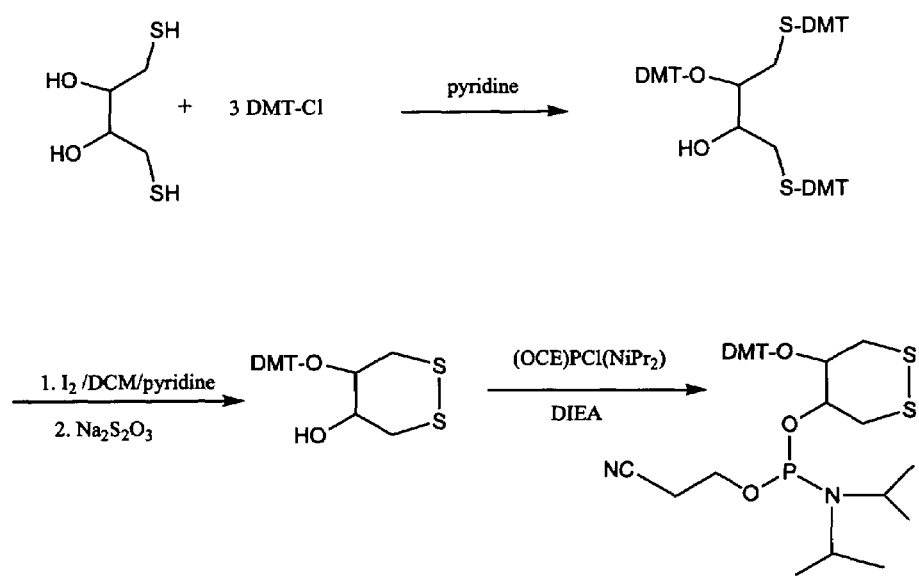

AA
Schutzgruppe—$Y^1$
            \\
             Z—$SR^1$
            /
         $Y^2$
            \\
             $SR^2$

2 Claims, 12 Drawing Sheets

OTHER PUBLICATIONS

Schepinov, M.S. et al. "Selectively cleavable synthetic oligodeoxyribonucleotides for the reversible immobilization of DNA" retrieved from STN Database accession No. 123:199284,CA XP002257908 & Bioorganicheskaya Khimiya Database CA (Online) Chemical Abstracts Service, Columbus, Ohio, U.S. 20 98-99, 955-66, 1994.

Kato, H. et al "Preparation of Glycerine Derivates for DNA Probes" retrieved from STN Database accession No. 121:134692 CA XP002257909 & JP 06 072990 A Toa Gosei Chem. Ind., Japan,, Database CA (online) Chemical Abstracts Service, Columbus, Ohio, US, 03-15, 1994.

* cited by examiner

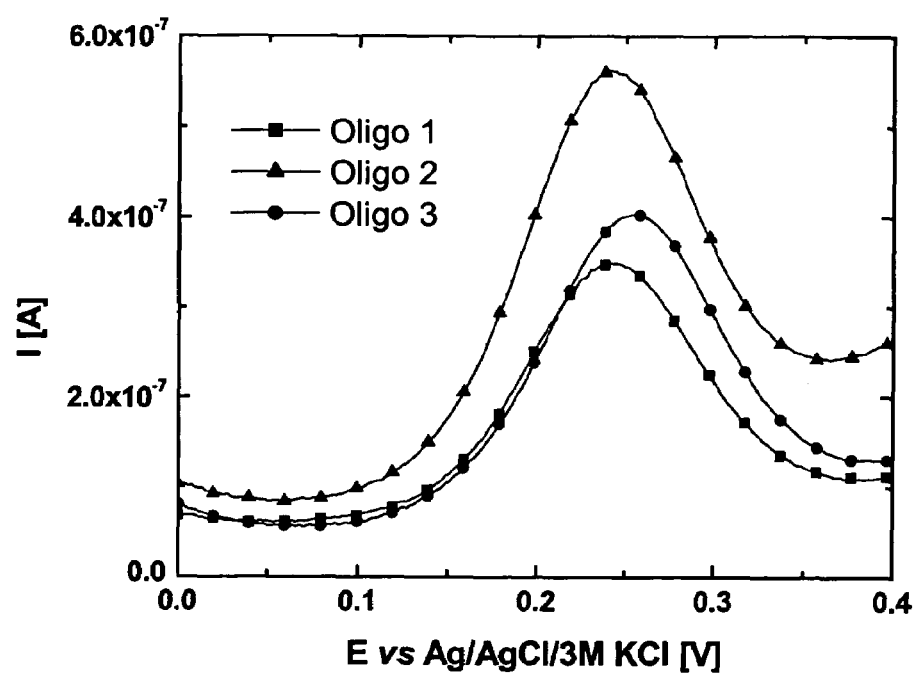
Fig 4.1

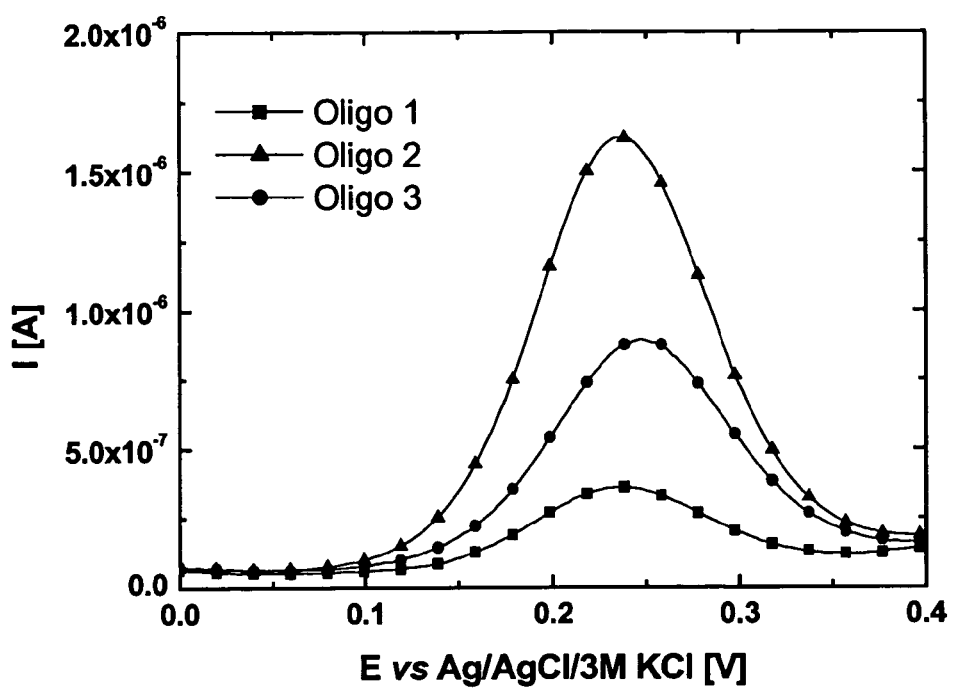
Fig 4.2

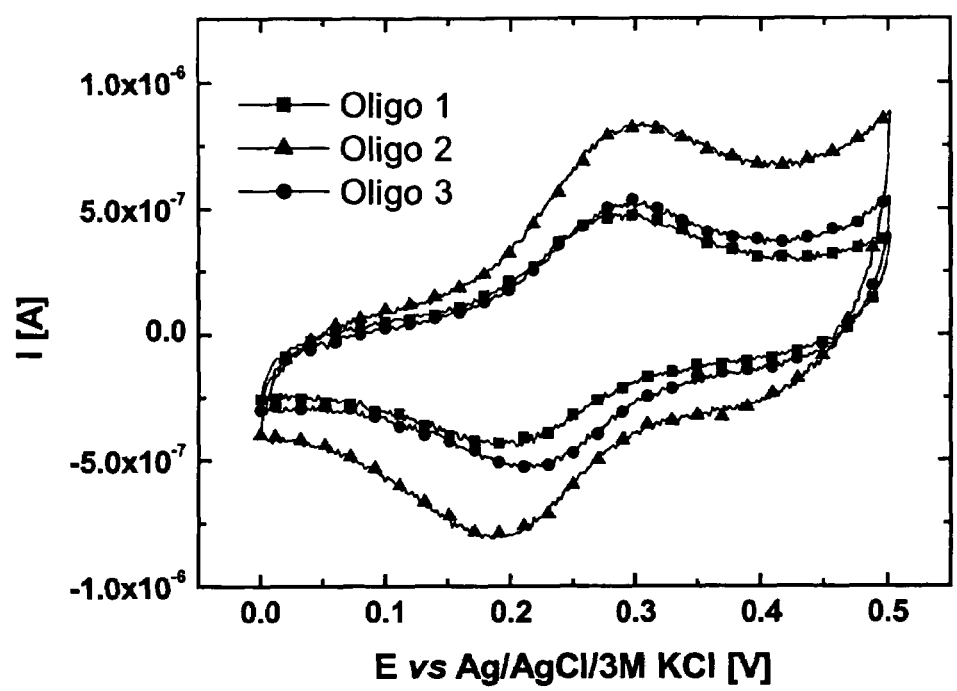
Fig 4.3

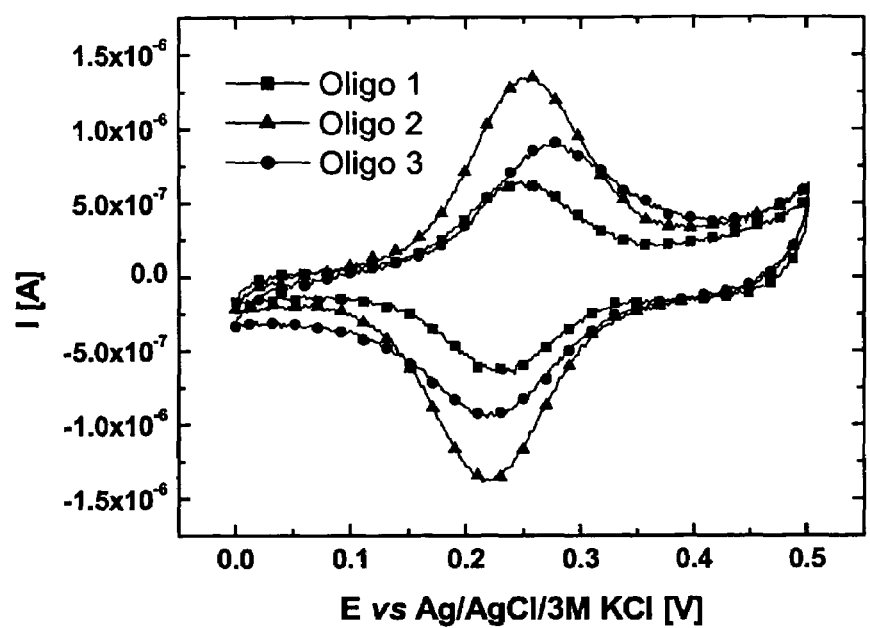
Fig 4.4

MULTIFUNCTIONAL REAGENT FOR THE SYNTHESIS OF THIOL MODIFIED OLIGOMERS

TECHNICAL FIELD

This invention concerns a multifunctional reagent for the synthesis of thiol modified oligomers.

STATE OF THE ART

Nucleic acids can be synthesized chemically or enzymatically. Depending on the Nucleotide building block used and the reaction step for coupling it to the next nucleotide in the sequence, different procedures can be distinguished: The phosphodiester method, the phosphotriester method and phosphoramidite method (Gait, M. J. et al., Oligonucleotide Synthesis: A Practical Approach, IRL Press Oxford, 1984; Protocols for Oligonucleotides and Analogs, Agrawal, S., Humana Press, New Jersey, 1993). The phosphoramidite method does not use derivatives of phosphoric acid, instead it uses derivatives of phosphorous acid, so called phosphoramidites.

The phosphoramidite method can be adapted to a solid phase method, where the growing nucleotide sequence is bound at a polymer carrier. This method considerably simplifies the separation of the excess synthesis reagents and building blocks as well as the purification of the oligonucleotide sequence. Commercially available synthesizers operate according to this principle.

Nucleic acids with known nucleotide sequences have a particular application in the specific detection of DNA in biological samples. In such tests the property of single nucleotide sequences are used, namely that they can form a double strand with their complimentary strand. The process of forming a double strand is called hybridization (Nucleic Acids in Chemistry and Biology, Blackburn, M. G. and Gait, J. M., Oxford University Press).

The formation of a double strand can be detected, if a modified single stranded complimentary nucleic acid is given for hybridisation to the single strand nucleic acid or the single stranded nucleic acid itself has a modification. Modifications can be i.e. fluorophores, radioisotopes or electro labels.

The application of marked targets for the detection of hybridization events has certain disadvantages. In the first place, the marking has to be done before the actual measurement. This requires an additional synthesis step and additional working time. Furthermore it is difficult to ensure a homogenous marking of the samples. Also, stringent washing is necessary to remove non bound or unspecific bound samples after hybridization.

Oligonucleotides and polymers in general can be immobilized on surfaces by well known methods i.e. by non covalent adsorption or by covalent couplings onto a surface (WO 00/42217; U.S. Pat. No. 6,312,906). Especially attractive procedures to immobilize oligonucleotides onto a $SiO_2$ surface (glass) are based on well established silicon chemistry (Parkam et al., Biochem. Biophys. Res. Commun., 1:1-6, 1978; Lund et al., Nucl. Acids Res. 16:10861-10880, 1988). For example epoxide modified $SiO_2$ surfaces can be coated by aminofunctionalized oligonucleotides.

The chemisorption on gold was investigated more closely from 1983. Nuzzo and Allara (J. Am. Chem. Soc. 105, 4481, 1983) discovered that thiol and disulfides adsorb on gold in ordered monolayers. The resulting covalent bond between gold and sulfur has a binding energy of 30-40 kcal/mol. Bain et al. (J. Am. Chem. Soc. 111, 321, 1989; J. Am. Chem. Soc. 111, 7155, 1989) described the property of the bonding between organo sulfur compounds and gold. The strong coordinative gold sulfur bonding advances the spontaneous accumulation of monolayers. Bain et al. argue that the formation of those monolayers are influenced by several factors (i.e. temperature, solvent, concentration and chainlength of the adsorbent and concentration of salt). The adsorption is comprised of two steps: The formation of a first monolayer coating about 80-90% of the surface is achieved within minutes, and the coating of the remaining area which requires a process lasting several hours. Displacements on the surface (i.e. solvent) and lateral diffusion probably play a role in that process. These experiments provide the foundation for the attachment of thiolmodified oligonucleotides.

Oligonucleotides attached onto the surface by one thiol bond, simply expressed by the term "Au—S-Oligonucleotide", are unstable under mechanical stress (i. e. washing steps). The stability of the oligonucleotide on the surface is increased by multiple formed Au—S-Bondings. A very stable attachment of the oligonucleotides brings enormous advantages for DNA Chip technology.

A variant for the attachment of DNA onto gold or platinum surfaces is provided by the developed process of Whitesides and co-workers (Lee et al., Pure & Appl. Chem. 63, 821, 1991) to generate thiol monolayers on gold surfaces. The free thiol group of a dithiol precoated metal surface (i.e. 1.10-Decandithiol) reacts with a bromacetyl modified oligonucleotide.

Sulfur containing phophoramidites or polymer carriers can be used for the production of thiol modified oligonucleotides. Examples of compounds for the coupling of disulfid units are the phosporamidite DMT-O—$(CH_2)_6$—S—S—$(CH_2)_6$—O—P(OCE)($NiPr_2$) or compounds of the general formula R1-S—S—$R^2$—O—P(OCE)($NiPr_2$) (see EP 523 978). Another possibility to couple a thiol anchor to an oligonucleotide is the use of the phosphoramidite MMT-S—$(CH_2)_6$—O—P(OCE)($NiPr_2$), however this has the disadvantage of the elaborate cleavage of the MMT group by $AgNO_3$.

In addition there are two further thiol carriers with C-3 and C-6 spacers for oligonucleotide synthesis (Glen Research).

In spite of the above described state of the art there is still a need for multifunctional thiol containing monomers able to form a polyfunctional thiol anchor, through which a stable attachment of molecules or polymers onto surfaces will be made possible.

DISCLOSURE OF THE INVENTION

The task of the present invention is to make thiol containing monomers available for the preparation of polyfunctional thiol compounds.

According to the invention the task is fulfilled by the compounds as stated in independent claim 1. Further attractive details, aspects and developments of the present invention follow from the dependent claims, the description, the figures and the examples.

In this presented invention the following abbreviations and terms will be used:
A: Adenine
ACN: Acetonitrile
Base: A, G, T, C or U
C: Cytosine
DMT: 4,4'-Dimethoxytrityl
DNA: Desoxyribonucleic Acid
$E^-$: Alternating Voltage
EI: Electrospray Ionisation
EtOAc: Ethylacetate Et$_3$N: Triethylamine
f: Alternating Voltage Frequency
Fmoc: 9-Fluorenylmethoxycarbonyl
G: Guanine
HPLC: Hoch Pressure Liquid Chromatography
iPr: Isopropyl
NMR: Nucleic Magnetic Resonance
M: Mass
MsCl: Mesylchloride or Methansulfonylchloride
MeOH: Methanol
MS: Mass Spectrometry
mV: Millivolt
$C_q$: Quarternary Carbon
$C_{arom}$: Aromatic Carbon
$H_{arom}$: Aromatic Hydrogen
$OD_{260}$: Optical Density (260 nm)
OCE: Cyanoethoxy
Oligomer: Equivalent to Nucleic Acid Oligomer
Oligonucleotide: DNA-, PNA- or RNA-Fragment with no specified chainlength of bases
PNA: Peptide Nucleic Acid (—NH—(CH$_2$)$_2$—N(COCH$_2$-Base)-CH$_2$CO; synthetic DNA or RNA in which the sugar phosphate unit is substituted by an amino acid. PNA can be hybridized with DNA or RNA).
RNA: Ribonucleic Acid
$R_f$: Retention at TLC relative to the solvent front
rms: root mean square
RP: Reverse Phase
s: Singlet
SPR: Surface Resonance Spectroscopy
T: Thymine
TCL: Thin Liquid Chromatography
U: Uracile
v: velocity of feed Every formula is to be interpreted in a way such that the corresponding chiral enantiomers are included.

The presented invention includes compounds of the formula (I)

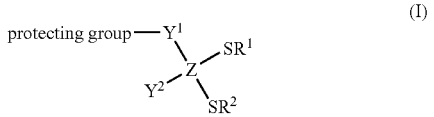

(I)

Where Z is a hydrocarbon of 2 to 28 C atoms, where Z can also include heteroatoms of the elements N, O, P, S, Si and halogen, R$^1$ and R$^2$ are the same or different H or sulfur protecting groups, where both S atoms could also form a disulfide bridge and in which case R$^1$, R$^2$ would not exist, protecting-group-Y$^1$, is protecting-group-NH, protecting-group-NR$^4$, protecting-group-O, CONH-protecting-group, protecting-group-OOC, protecting-group-S—S, —CH(protecting-group-O)$_2$, or —CR$^5$(protecting-groupO)$_2$ or protecting-group-S, Y$^2$ is —OH, —NH$_2$, —NHR$^3$, —NR$^3$R$^4$, —COOH, —COCl, —COOCO—R$^6$, —CONH$_2$, —CONHR$^3$, —COOR$^3$, —SO$_3$H, —SO$_3$Cl, —SH, —S—SR$^3$, —CHO, —COR$^3$, —C$_2$H$_3$O, halogen, —N$_3$, —NH—NH$_2$, —NCO, —NCS, where R$^3$ is alkyl, heteroalkyl, aryl, cycloalkyl or a protecting group, where R$^3$ can be the same or different in the groups Y$^1$ and Y$^2$, R$^4$ is a protecting group, where R$^4$ can be the same or different in the groups Y$^1$ and Y$^2$, and where R$^4$ and R$^3$ can be the same or different, R$^5$ is alkyl, aryl, cycloalkyl, where R$^5$ can be the same or different in the groups Y$^1$ and Y$^2$ and R$^5$ is alkyl, heteroalkyl, aryl, or cycloalkyl, where R$^6$ can be the same or different in the groups Y$^1$ and Y$^2$, where Y$^2$ can also be a group of the formula (II) or (III),

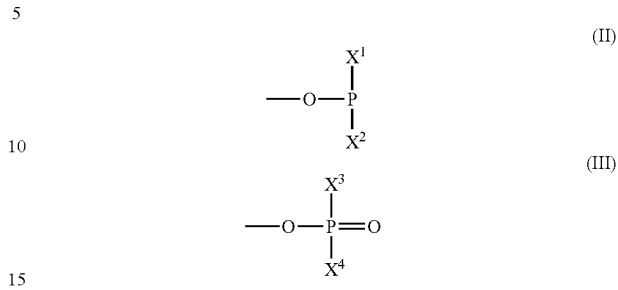

Where X$^1$ is a halogen or a substituted amine, X$^2$ is alkyl, alkoxy, aryloxy or a cyano derivative of alkyl, alkoxy, aryloxy, X$^3$ is a halogen, an amino group or oxygen and X$^4$ is alkyl, alkoxy, aryloxy or X$^4$ is H where X$^3$ is oxygen.

The invented compounds are substances consisting of at least four functional groups, of which two are thiols (R$^1$, R$^2$=H), thioethers or disulfides, where both sulfur atoms can be joined together to form a disulfide bridge and R$^1$, R$^2$ do not exist. Y$^1$ is a functional group with a protecting group. Y$^2$ is a functional group, which serves amongst other things for the activation of the invented compounds for chemical reactions. Such chemical reactions are for example a polymerisation or an attachment to a polymeric carrier material. Where Y$^2$ can be an already activated functional group or a to be activated functional group. The fundamental body Z is a structure of hydrocarbon consisting of 2 to 28 atoms, where Z can also include heteroatoms of the elements N, O, P, S, Si and halogen. The compounds of formula (I) have at least one protecting group.

The invented compounds can be used for the directed and defined construction of oligomers, or polymers with an exactly defined number of sulfur atoms. For which the selective cleavage of a protecting group is a necessary prerequisite. The chemical reaction of the monomers must not influence the integrity of the protecting group. The existing R$^1$, R$^2$ at the sulfur must be chemically stable during polymerisation which includes the activation of the functional group and the cleavage of the protecting group: This means the protecting group at Y$^1$, has to be orthogonally or selectively cleavable to R$^1$, R$^2$ at the sulfur.

Should R$^1$ and R$^2$ not exist and as a result the two sulfur atoms are joined together to form a disulfide bridge, the fact that the disulfide unit is not located in the backbone of the polymer represents a special advantage in that a cleavage of the disulfide bridge/s does not cause a destruction of the polymer.

Protecting groups can be amongst others triphenylmethyl-, t-butoxycarbonyl-, benzyl-, 2,4dinitrophenyl-, 9-fluorenylmethoxycarbonyl-, allyloxycarbonyl-, benzyloxymethyl-, acetyl-, 4azidobenzyloxycarbonyl-, acetamidomethyl-, 1-adamantyl-, 1-adamantyloxycarbonyl-, anisyl, benzamidomethyl-, biphenyldimethylsilyl-, 2,4dimethylthiophenoxycarbonyl-, 1-methyl-1-(4-biphenyl)ethoxycarbonyl-, benzothiazole-2-sulfonyl-, t-butoxymethyl-, benzoyl-, benzyloxycarbonyl-, cyclohexan-1,2-diacetal-, cyclohexyl-, 2-(4,4-dimethyl-2,6-dioxocyclohexylidene)ethyl-, 1-methyl-1-(3,5-dimethoxyphenyl)ethoxycarbonyl-, diethylisopropylsilyl-, 1,3-dithianyl-2-methyl-, 2,4dimethoxybenzyl-, dithianylmethoxycarbonyl-, dimethoxytrityl-, p,p'-dinitrobenzhydryl-, 2,4-dinitrophenyl-, 2,4dimethylpent-3-yloxycarbonyl-, 2-(diphenylphosphino)ethyl-, 9-fluorenylmethyl-, levulinoyl-, p-methoxybenzensulfonyl-, 2,6-dimethoxy-4-methoxybenzensulfonyl-, monomethoxytrityl-, methoxyphenylsulfonyl-, mesitylensulfonyl-, o-nitrobenzyl-, 2-[2-(benzyloxy)ethyl]benzoyl-, 3-(3-pyridyl)allyloxycarbonyl-, 2,2,5,7,8-pentamethylchroman-6-sulfonyl-, pivaloyloxymethyl-, t-butyidimethylsilyl-, t-butyldiphenylsilyl-, 2,2,2-trichloro-1,1-dimethylethyl-, trifluoroacetyl-, triisobutylsilyl-, 2,4,6-trimethylbenzyl-, trimethoxybenzyl-, p-toluensulfonyl- or benzyloxycarbonyl-. Further protecting groups can be found in Greene, T. W., Protective Groups in Organic Synthesis, Wiley-Interscience, 1999.

$R^1$ and $R^2$ are identical or disparate sulfur protecting groups, which can be amongst others derivatives of benzyl, triphenylmethyl, substituted methyl, benzoyl-, trifluoracetyl- or t-butoxycarbonyl-groups. In addition the thiols can be protected as disulfides i.e. S-ethylsulfides, S-phenyldisulfides or as thiocarbamates. Further protecting groups can be found in Greene, T. W., Protective Groups in Organic Synthesis, Wiley-Interscience, 1999.

All of the invented compounds can be incorporated in oligomers as monomer units.

The invented compounds can be singly or multiply attached, independently of the position in the nucleotide oligomers, peptide oligomers or other molecules. Therefore for example the attachment of any molecule and also polymers onto a surface or at a polymer carrier using a polythiol anchor is possible. By the activation of the polyfunctional thiol anchor multiple attachments of the molecule onto the surface (i.e. gold surface) or to another polymer carder are formed. For this special preactivated surfaces (i.e. surfaces activated by aldehyde or maleimide) or special polymer compounds having thiol reactive groups for example peptides, proteins, PNA, RNA, LNA (locked nucleic acids) can be used. Those invented compounds that are attached at molecules or in particular at polymers can also be used for the attachment of markers (labels) or other functionalities at molecules or in particular at polymers.

An advantage of the invented compounds is the possibility to incorporate multiple SH groups into oligomers thereby generating higher stability through the immobilization of the oligomers onto a surface. Further advantage is the possibility to couple various molecules i. e. polymers, peptides, proteins or oligonucleotides at a polymer with multiple SH-groups.

$Y^2$ can also be coupled direct or via a linker to a solid carrier material i.e. CPG (controlled pore glass), microbeads, polymers (i.e. polystyrene) or membranes. To synthesize nucleic acids, the invented compounds will normally be attached to an solid carrier via an aminoalkyl (LCM=long chain alkyl amine).

The preferred in the context of the presented invention reactive phosphor intermediates can be singly or multiply incorporated at the 3' end, in the middle and at the 5' end of an oligonucleotide. By activation a multiple polyfunctional thiol anchor can be liberated, which can be used for a multiple attachment for example of an oligonucleotide onto a surface; onto preactivated surfaces (i.e. aldehyde, maleimide), or at other polymer compounds (i.e. proteins, PNA, RNA, LNA) having groups reactive to thiols. Furthermore this polyfunctional polythiol anchor can be used for the directed multiple attachment of markers and ligands to molecules or polymers. Markers and ligands may be for example ezymatic, chromogene, fluorogene, radioactive, chemiluminiscent labels, in nucleic acids oligomers intercalating agents, metals, metal ions, drugs, hormones, proteins, peptides, nucleolytic or proteolytic agents, especially binding agents (like i.e. biotin, antigenes, haptenes, antibodies, receptors) and other compounds of biological interest, which i.e. influence the transport through biological membranes or change the solubility of oligonucleotides. There are known procedures, which make it possible to couple these ligands and markers to thiol groups such as for example by maleimides. aldehydes and halogenacetyl compounds (Means, G. M. and R. E. Feeney, Chemical Modification of Proteins, Holden-Day Inc., 1971; Feeney, R. E., Int. J. Peptide Protein Res., 29: 145-161, 1987; Eritja, R. et al., Tetrahedron, 47, 4113-4120, 1991).

The bonding between the surface and the oligonucleotide via one thiol anchor, simplified as surface-S-oligonucleotide, is not stable to mechanical stress, for example during washing steps. One of the advantages of the presented invention is the possibility to couple a poly anchor at an oligonucleotide, such that the attachment of the oligonucleotide to gold is optimised by several Au—S-bondings. In which case the conditions for the attachment onto the surface for example the concentration of salt used, the applied potential at the surface or the kind of premodificated surface are crucial. Furthermore thiols already deposited on the surface can be displaced by this poly anchor.

Furthermore the deprotection of the sulfur protecting group by AgNO3 is avoided by the use of DMT as the protecting group. The DMT protecting group can be cleaved by mild acid treatment, which is compatible with oligonucleotide chemistry. The presented invented compounds can be used under the usual standard conditions for oligonucleotide chemistry.

The phosphorous containing compounds include intermediates that can be used in the H-phosphonate, phosphotriester, phosphorchloridite and phosphoramidite methods of oligonucleotide synthesis. Furthermore these intermediates can include phosphodiester analogs such as methyl phosphonates, methyl phosphates, phosphorthioates and phosphoramidites (EP 0 523 978), for modifications at 5'-, 3' end and/or in the sequence.

According to a preferred embodiment of the invention $Y^2$ is equivalent to formula II or III, in which $X^1$ is a halogen and $X^2$ is methyl or $R^7O$—, where $R^7$ is alkyl, cycloalkyl, aryl or a cyano derivative of alkyl, aryl, or $X^2$ is equivalent to $R^7O$— and $X^1$ is equivalent to —$NR^8R^9$, where $R^8$ and $R^9$ are independently from each other alkyl, heteroalkyl, cycloalkyl, aryl or $R^8$ and $R^9$ are joined together to form with the N atom a cyclic structure of 4 to 7 C atoms, in which one C atom of the cyclic structure can be replaced by O or S, or $X^3=O^-$ and $X^4=H$ or is $R^{10}O$—, in which $R^{10}$ is a protecting group.

The presented invented compounds can also be bound to a carrier material (solid support), if Z possesses a free or a protected OH function. A wide selection of carrier materials can be used, for instance silica, Porasil C, polystyrene, Controlled Pore Glass (CPG), Kieselgur, poly(dimethylacrylamide), poly(acrylmorpholino), Cellulose, Fractosil 500. Depending on the type of carrier materials different functionalities for the anchor are used. Substituted alkyl or aryl silyl compounds are used for silicon carrier materials like Silica and glass to form a siloxan or siloximine anchor. Ethers, esters, amines, amides, sulfides, sulfones and phosphates can be used by organic polymers.

In the case that $Y^2$ is a group of the formula (III), in which $X^3$ is equivalent to $O^-$ and $X^4$ is equivalent to H, the above mentioned compounds represent H-phosphonates and are employed in the H-phosphonate method for the oligonucleotide synthesis (Sinha und Cook, Nucleic Acids Research (1988) 16:2659-2669). H-phosphonates may be converted to phosphit diesters, phosphorothioates, or phosphoramidates, as soon they are incorporated at the 5' end of the oligonucleotide (Miller et al., Nucleic Acids Res. (1983) 11:5189-5204, Eckstein, Ann. Rev. Biochem. (1985) 54:367-402).

Accordingly, the above mentioned compounds in which $Y^2$ is a group of the formula (III) in which $X^3$ is equivalent to $O^-$ and $X^4$ is equivalent to $R^{10}O$— can be used in the phosphotriester method for oligonucleotide synthesis (Garegg, et al., Chemica Scripta (1985) 26:5).

The compounds in which $Y^2$ represents a group of the formula (II), in which $X^1$ is equivalent to chlorine and $X^2$ is equivalent to $R^7O$—, are phosphochloridites and are used in the phosphochloridite technique for oligonucleotide synthesis (Wada et al., J. Org. Chem. (1991) 56:1243-1250).

The phosphoramidites in which $Y^2$ is equivalent to the above formula (II) are especially preferred for the purpose of the presented invention.

$R^1$ and $R^2$ are the same or different H or sulfur protecting groups. Preferred sulfur protecting groups are for example trityl, 4,4'-dimethoxytrityl, 4-monomethoxytrityl, 9-fluorenylmethyl (Ponsati, B., et al., Tetrahedron, 46, 8255-8266, 1990), 9-fluorenylmethoxycarbonyl, 2,4-dinitrophenylethyl, 2,4,6-trimethoxybenzyl (Munson, M. C. et al., J. Org. Chem., 57, 3013-3018, 1992), 4-methoxybenzyl and allyloxycarbonylaminomethyl (Kimbonguila, A. M., et al., Tetrahedron 55, 6931-6944, 1999). Especially preferred is 4,4'-dimethoxytrityl. Further protecting groups can be found in Lloyd-Williams, P. et al., Chemical Approaches to the Synthesis of Peptides and Proteins, New York, CRC Press. The sulfur protecting groups trityl and acetamidomethyl can be cleaved by iodine oxidation (Kamber et al., Helvetica Chimica Acta, Vol. 63, No. 96, 899-915, 1980). The sulfur protecting groups 4,4'-dimethoxytrityl and 4-monomethoxytrityl can be cleaved by $AgNO_3$ in methanol (Huang, Z. and Benner, S. A., Synlett, 83-84, 1993). The 4,4'-dimethoxytrityl sulfur protecting group can also be cleaved under mild acid conditions (i.e. 2% dichloro acetic acid in dichloromethane), that is compatible to the oligonucleotide synthesis. The great variety of sulfur protecting groups offers the opportunity to select orthogonal protecting groups, whose deprotection conditions are compatible to the oligonucleotide synthesis to introduce different labels.

According to a preferred embodiment of the presented invention the rest $R^7$ represents a base labile protecting group.

In a particularly preferred embodiment $R^7$ is a base labile protecting group selected from β-cyanoethyl, β-nitroethyl, 2,2,2-trichlorethyl, methyl, 1,1-dimethyl-2,2,2-thrichlorethyl, 2,2,2-tribromethyl, benzyl, o-chlorphenyl, p-nitrophenylethyl, 2-methylsulfonylethyl and 1,1-dimethyl-2-cyanoethyl.

According to an especially preferred embodiment of the presented invention where $R^7$ is a base labile protecting group $R^8$ and $R^9$ are individually alkyl consisting of 1 to 16 C atoms, cycloalkyl consisting of 3 to 8 C atoms, aryl consisting of 6 to 20 C atoms; or $R^8$ and $R^9$ are joined together to form with a N atom a cyclic structure with 4 to 7 C atoms, in which a C atom of the cyclic structure can be replaced by O or S. Moreover it is especially preferred, if $R^8$ and $R^9$ are independently from each other alkyl consisting of 1 to 6 C atoms. Also especially preferred is where $R^8$ and $R^9$ are isopropyl, butyl, hexyl, nonyl, dodecyl, hexadecyl, cyclopropyl, cyclobutyl, cyclohexyl, cyclooctyl, phenyl, tolyl, benzyl, xylyl, naphthyl, morpholino, piperidinyl or thiomorpholino.

Further protecting groups $R^8$ and $R^9$ are listed in Green, T. W., Protective Groups in Organic Chemistry, New York: Wiley & Sons, 1981.

According to a preferred embodiment of the presented invention, Z is a hydrocarbon structure consisting of 2 to 28 C atoms, in which Z also includes the heteroatoms of the elements N, O, P and S.

According to a further preferred embodiment of the presented invention, Z is a hydrocarbon structure consisting of 2 to 28 C atoms, in which Z also includes the heteroatoms of the elements N, O and P.

According to a further preferred embodiment of the presented invention, Z is a hydrocarbon structure consisting of 2 to 28 C atoms, in which Z also includes the heteroatoms of the elements N and O.

According to a further preferred embodiment of the presented invention, Z is a hydrocarbon structure consisting of 2 to 28 C atoms, where Z can also include the heteroatoms of the elements N and O, in which the elements N and O are solely present as part of an amide bond.

According to a further preferred embodiment of the presented invention, Z is a hydrocarbon structure consisting of 2 to 28 C atoms, in which Z also includes the heteroatoms of the elements P and O.

According to a further preferred embodiment of the presented invention, Z is a hydrocarbon structure consisting of 2 to 28 C atoms, where Z can also include the heteroatoms of the elements P and O, in which the elements P and O are solely present as part of a phospor diester bond.

According to a further preferred embodiment of the presented invention, Z is a hydrocarbon structure consisting of 2 to 8 C atoms.

According to an especially preferred embodiment of the presented invention, Z is a hydrocarbon structure consisting of 4 C atoms and 6 H atoms.

According to an especially preferred embodiment of the presented invention compounds of the formula

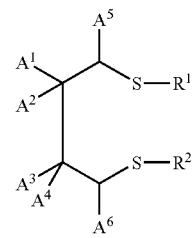

(IV)

are provided, where $A^1$, $A^2$, $A^3$, $A^4$, $A^5$, $A^6$ are the same or different alkyl of 1-22 C atoms, heteroalkyl of 1-22 C atoms, cycloalkyl of 1-22 C atoms, H, protecting-group-$Y^1$ or group $Y^2$, where $A^1$, $A^2$, $A^3$, $A^4$, $A^5$, $A^6$ can also include protecting-group-$Y^1$ and group $Y^2$ and where protecting-group $Y^1$ as well as group $Y^2$ is present at least once.

The compounds according to formula (IV) possess at least two further functional groups besides both S atoms. Moreover the substitutes $A^1$, $A^2$, $A^3$, $A^4$, $A^5$ and $A^6$ can be a functional group. $A^1$, $A^2$, $A^3$, $A^4$, $A^5$ and $A^6$ can also be alkyl of 1-22 C atoms, heteroalkyl of 1-22 C atoms or H, in the case that out of the six substitutes $A^1$, $A^2$, $A^3$, $A^4$, $A^5$ and $A^6$ not less than two of the substitutes are functional groups, at least the missing functional group(s) must be bound to the above defined heteroalkyl(s). At least one of these functional groups is protected by a protecting group.

Preferred are compounds, where $A^2$ and $A^4$ are equal to protecting-group-$Y^1$ or $Y^2$, where $A^2$, $A^4$ can also include protecting-group-$Y^1$ and group $Y^2$ and where protectinggroup-$Y^1$ as well as group $Y^2$ are present at least once. In the case that compounds of the structure (IV) are present, where $A^1$, $A^3$, $A^5$ and $A^6$ are alkyl of 1-22 C atoms, heteroalkyl of 1-22 C atoms, cycloalkyl of 1-22 C atoms or H. $A^2$ and $A^4$ are functional groups or include a functional group. The substitute, which is not a functional group, is a heteroalkyl of 1-22 C atoms or a cycloheteroalkyl of 1-22 C atoms including at least one functional group. At least one of these functional groups is protected by a protecting group. Should $A^2$ or $A^4$ include two functional groups, the substitute not including a functional group can be an alkyl of 1-22 C atoms, heteroalkyl of 1-22 C atoms, cycloalkyl of 1-22 C atoms or H.

Especially preferred are compounds, where $A^2$, $A^4$ are identical to protecting-group-$Y^1$, $Y^2$, where $A^2$ is not identical to $A^4$. In that case compounds of the structure (IV) are present, where $A^1$, $A^3$, $A^5$ and $A^6$ are alkyl of 1-22 C atoms, heteroalkyl of 1-22 C atoms, cycloalkyl of 1-22 C atoms or H. $A^2$ and $A^4$ are functional groups. At least one of these functional groups is protected by a protecting group.

Especially preferred are compounds, where $A^1$, $A^3$, $A^5$ and $A^6$ are identical to H. In that case compounds of the structure (IV) are present, where $A^1$, $A^3$, $A^5$ and $A^6$ are H and $A^2$ and $A^4$ are a functional group. At least one of these functional groups is protected by a protecting group.

Also preferred are compounds of the structure (IV), where protecting-group-$Y^1$ is identical to protecting-group-OOC, protecting-group-O, protecting-group-S, protecting-group-NH or protecting-group-$NR^y$ and $Y^2$ is identical to COOH, $COOR^x$, OH, $OR^x$, SH, $SR^x$, $NH_2$, $NHR^x$, $NR^xR^y$, where $R^x$ is a protecting group and $R^y$ is an alkyl of 1-15 C atoms, an aryl of 1-14 C atoms, a cycloalkyl of 1-15 C atoms, a heteroalkyl of 1-15 C atoms, a protecting group or a group of the formula (II) or (III).

Most especially preferred are compounds of the structure (IV), where $A^2$ is identical to protecting-group-O, protecting-group-OOC or protecting-group-NH, where $A^4$ is identical to COOH, a group of the formula (II) or (III) or protecting-group-NH, and $R^1=R^2$=DMT or both S atoms are joined together to form a disulfide bridge and in that case $R^1$, $R^2$ do not exist.

According to an especially preferred embodiment of the presented invention compounds of the formula

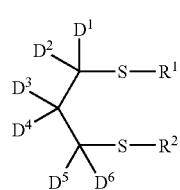

are provided, where $D^1$, $D^2$, $D^3$, $D^4$, $D^5$, $D^6$ are the same or different alkyl of 1-22 C atoms, heteroalkyl of 1-22 C atoms, cycloalkyl of 1-22 C atoms, H, protecting-group-$Y^1$ or group $Y^2$, where $D^1$, $D^2$, $D^3$, $D^4$, $D^5$, $D^6$ can also include protecting-group-$Y^1$ and group $Y^2$ and where protecting-group-$Y^1$ as well as group $Y^2$ is present at least once.

In addition to containing both S groups, compounds according to formula (V) have at least two further functional groups. Moreover the substitutes $D^1$, $D^2$, $D^3$, $D^4$, $D^5$ and $D^6$ can be a functional group. $D^1$, $D^2$, $D^3$, $D^4$, $D^5$ and $D^6$ can also be alkyl of 1-22 C atoms, heteroalkyl of 1-22 C atoms, cycloalkyl of 1-22 C atoms or H, in the case that out of the six substitutes $D^1$, $D^2$, $D^3$, $D^4$, $D^5$ and $D^6$ not less than two of the substitutes are functional groups, at least the missing functional group(s) must be bound to the above defined heteroalkyl(s). At least one of these functional groups is protected by a protecting group. $R^1$ and $R^2$ are as defined above.

Also preferred are compounds of the structure (V), where $D^1$, $D^3$ and $D^5$ are alkyl of 1-22 C atoms, heteroalkyl of 1-22 C atoms, cycloalkyl of 1-22 C atoms or H. The substitutes $D^2$, $D^4$, $D^6$ can be a functional group. $D^2$, $D^4$ and $D^6$ can also be alkyl of 1-22 C atoms, heteroalkyl of 1-22 C atoms or cycloalkyl of 1-22 C atoms or H, in the case that out of the three substitutes $D^2$, $D^4$ and $D^6$ not less than two of the substitutes are functional groups, at least the missing functional group(s) must be bound to one of the above defined heteroalkyl(s). At least one of these functional groups is protected by a protecting group.

Also preferred are compounds of the structure (V), where $D^2$ or $D^4$ or $D^6$ is identical to protecting-group-$Y^1$ or $Y^2$ and $D^2$ or $D^4$ or $D^6$ include the groups protecting-group-$Y^1$ or $Y^2$, where protecting-group-$Y^1$ as well as group $Y^2$ are present at least once.

Also preferred are compounds of the structure (V), where $D^1$, $D^2$, $D^3$ and $D^5$ are identical to H and $D^4$ and $D^6$ include the groups protecting-group-$Y^1$ and $Y^2$.

Also preferred are compounds of the structure (V), where protecting-group-$Y^1$ is identical to protecting-group-OOC, protecting-group-O, protecting-group-S, protecting-group-NH or protecting-group-$NR^y$ and $Y^2$ is identical to COOH, $COOR^x$, OH, $OR^x$, SH, $SR^x$, $NH_2$, $NHR^x$ or $NR^xR^y$, where $R^x$ is a protecting group and $R^y$ is an alkyl of 1-15 C atoms, an aryl of 1-14 C atoms, a cycloalkyl of 1-15 C atoms, a heteroalkyl of 1-15 C atoms, a protecting group or a group of the formula (II) or (III).

Also preferred are compounds of the structure (V), where $D^1$, $D^2$, $D^3$ and $D^5$ are identical to H and $D^4$ and $D^6$ are protecting-group-$Y^1$, $Y^2$.

Also preferred are compounds of the structure (V), where $D^1$, $D^2$, $D^3$, $D^4$ and $D^5$ are identical to H and $D^5$ is heteroalkyl of 1-22 C atoms or cycloheteroalkyl of 1-22 C atoms, where $D^6$ include the groups protecting-group-$Y^1$ and $Y^2$, where $R^1=R^2$=DMT or both S atoms are joined together to form a disulfide bridge and in that case $R^1$, $R^2$ do not exist.

Also especially preferred are compounds of the structure (V), where $D^1$, $D^2$, $D^3$ and $D^5$ are H. $D^4$ or $D^6$ are a functional group. The substitute that is not a functional group is a heteroalkyl of 1-22 C atoms or a cycloheteroalkyl of 1-22 C atoms with at least one functional group. At least one of these functional groups is protected by a protecting group.

Also especially preferred are compounds of the structure (V), where $D^1$, $D^2$, $D^3$ and $D^5$ are H. The substitutes $D^4$ and $D^6$ are alkyl of 1-22 C atoms, heteroalkyl of 1-22 C atoms, cycloalkyl of 1-22 C atoms or H, with the restriction that at least two functional groups are bound amongst $D^4$ and $D^6$. At least one of these functional groups is protected by a protecting group.

Especially preferred are the functional groups COOH, $COOR^x$, OH, $OR^x$, SH, $SR^x$, $NH_2$, $NHR^x$ and $NR^xR^y$, where $R^x$ represents a protecting group and $R^y$ is alkyl of 1-15 C atoms, heteroalkyl of 1-15 C atoms, aryl of 1-14 C atoms, cycloakyl of 1-15 C atoms, or a protecting group, which can be cleaved independently of $R^{x3}$ or a group of the formula (II) or (III).

Most especially preferred are compounds of the structure (V), where $D^1$, $D^2$, $D^3$, $D^4$ and $D^5$ are H. $D^6$ is a hteroalkyl of 1-22 C atoms or a cycloheteralkyl of 1-22 C atoms including a total of at least two functional groups, at least one of which is protected by a protecting group. The functional groups are a group of formula (II) or $OR^x$, $COOR^x$, COOH or $NHR^x$, where $R^x$ is DMT, Fmoc or an alkyl of 1-22 C atoms. $R^1=R^2=$DMT or $R^1$ and $R^2$ do not exist, if both S atoms are joined together to form a disulfide bridge.

According to an especially preferred embodiment of the presented invention compounds of the formula

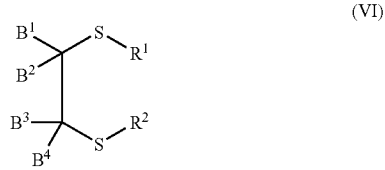

(VI)

are provided, where $B^1$, $B^2$, $B^3$ and $B^4$ are identical or different alkyl of 1-22 C atoms, heteroalkyl of 1-22 C atoms, cycloalkyl of 1-22 C atoms, H, protecting-group-$Y^1$ or group $Y^2$, where $B^1$, $B^2$, $B^3$ and $B^4$ can also include protecting-group-$Y^1$ and group $Y^2$ and where protecting-group-$Y^1$ as well as group $Y^2$ is present at least once.

In addition to containing both S groups, compounds of formula (VI) have at least two further functional groups. Further the substitutes $B^1$, $B^2$, $B^3$, $B^4$ can be a functional group. $B^1$, $B^2$, $B^3$ and $B^4$ can also be alkyl of 1-22 C atoms, heteroalkyl of 1-22 C atoms, cycloalkyl of 1-22 C atoms or H, in the case that out of the four substitutes $B^1$, $B^2$, $B^3$, $B^4$ not less than two of the substitutes are functional groups, at least the missing functional group(s) must be bound to the above defined heteroalkyl(s). At least one of these functional groups is protected by a protecting group.

Especially preferred are compounds of the structure (VI), where $B^2$ or $B^4$ is identical to protecting-group-$Y^1$ or $Y^2$ and either $B^2$ or $B^4$ include the groups protecting-group-$Y^1$ or $Y^2$, where protecting-group-$Y^1$ as well as group $Y^2$ are present at least once.

Also especially preferred are compounds of the structure (VI), where $B^1$, $B^2$ and $B^3$ are identical to H and $B^4$ include the groups protecting-group-$Y^1$ and $Y^2$.

Also especially preferred are compounds of the structure (VI), where $B^4$ is a heteroalkyl of 1-22 C atoms or a cycloheteroalkyl of 1-22 C atoms, where $B^4$ includes the groups protecting- group-$Y^1$ and $Y^2$, where protecting-group-$Y^1$ is identical to protecting-group-OOC, protecting-group-O or protecting-group-NH and $Y^2$ is identical to COOH, COOR$^x$, OR$^x$, NHR$^x$ or a group of formula (II), where R$^x$ is identical to DMT or Fmoc and $R^1=R^2=$DMT or both S atoms are joined together to form a disulfide bridge and in that case $R^1$, $R^2$ do not exist.

Also especially preferred are compounds of the structure (VI), where $B^1$ and $B^3$ are alkyl of 1-22 C atoms, heteroalkyl of 1-22 C atoms, cycloalkyl of 1-22 C atoms or H. $B^2$ and $B^4$ are a functional group. At least one of these functional groups is protected by a protecting group.

Also especially preferred are compounds of the structure (VI), where $B^1$ and $B^3$ are alkyl of 1-22 C atoms, heteroalkyl of 1-22 C atoms, cycloalkyl of 1-22 C atoms or H. $B^2$ or $B^4$ are functional groups. The substitute that is not a functional group is a heteroalkyl of 1-22 C atoms or a cycloheteroalkyl of 1-22 C atoms with at least one functional group. At least one of these functional groups is protected by a protecting group.

Also especially preferred are compounds of the structure (VI), where $B^1$ and $B^3$ are alkyl of 1-22 C atoms, heteroalkyl of 1-22 C atoms, cycloalkyl of 1-22 C atoms or H. The substitutes $B^2$ and $B^4$ are alkyl of 1-22 C atoms, heteroalkyl of 1-22 C atoms, cycloalkyl of 1-22 C atoms or H, with the restriction that at least two functional groups are bound amongst $B^2$ and $B^4$. At least one of these functional groups is protected by a protecting group.

Also especially preferred are compounds of the structure (VI), where $B^1$, $B^2$, $B^3$ are H. $B^4$ is a heteroalkyl of 1-22 C atoms or a cycloheteroalkyl of 1-22 C atoms including a total of at least two functional groups, of which at least one is protected by a protecting group. The functional groups are COOH, COOR$^x$, OH, OR$^x$, SH, SR$^x$, NH$_2$, NHR$^x$, NR$^x$R$^y$, where R$^x$ represents a protecting group and R$^y$ is alkyl of 1-15 C atoms, heteroalkyl of 1-15 C atoms, aryl of 1-14 C atoms, cycloalkyl of 1-15 C atoms or a protecting group, which can be cleaved independently of R$^x$ or a group of formula (II).

Also especially preferred are compounds of the structure (VI), where $B^1$, $B^2$, $B^3$ are H. $B^4$ is a heteroalkyl of 1-22 C atoms or a cycloheteroalkyl rest of 1-22 C atoms including a total of at least two functional groups, of which at least one is protected by a protecting group. The functional groups are a group of formula (II) or OR$^x$, COOR$^x$, COOH or NHR$^x$, where R$^x$ is DMT, Fmoc or an alkyl of 1-22 C atoms. $R^1=R^2=$DMT or $R^1$ and $R^2$ are not present, if both S atoms are joined together to form a disulfide bridge.

The presented invention includes also the application of the invented compounds for the modification of oligomers. In addition the presented invention also includes the application of the invented compounds for the immobilisation of modified oligomers on surfaces. Furthermore the presented invention also includes the application of the invented compounds for the conjugation of enzymatic, chromogene, fluorogene, radioactive or chemiluminiscent labels, substances intercalating in nucleic acids, metals, metal ions, hormones, proteins, peptides, nucleolytic and proteolytic agents, biotin, antigens, haptens, antibodies or receptors to molecules or oligomers. Finally the invention also includes the application of the invented compounds for the automatic synthesis of oligomers.

Within the described applications of the invented compounds it is especially preferred that the oligomers used are oligonucleotides, polypeptides, PNA or LNA (Locked Nucleic Acid).

The synthesis of oligonucleotides which are modified with the invented compounds takes place in solution or preferably at solid phase, if necessary using an automated synthesiser.

A SHORT DESCRIPTION OF THE DRAWINGS

Figure 2:
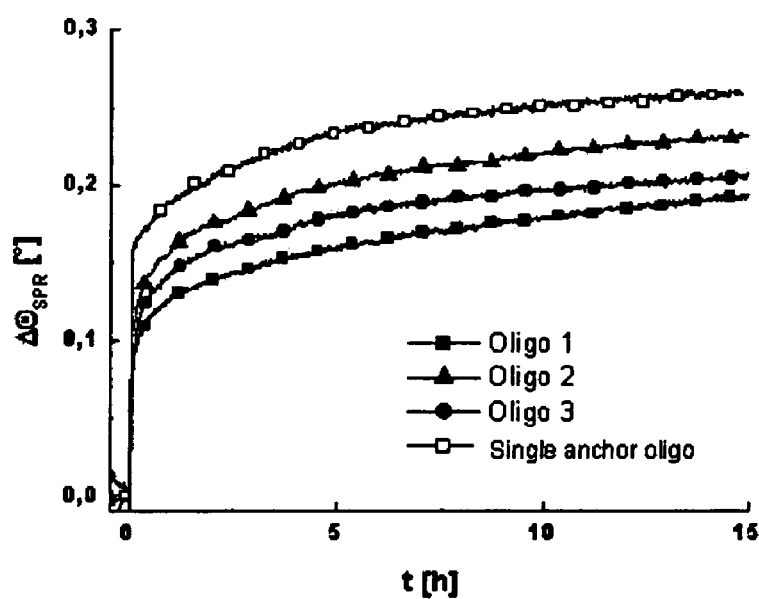
Figure 3:
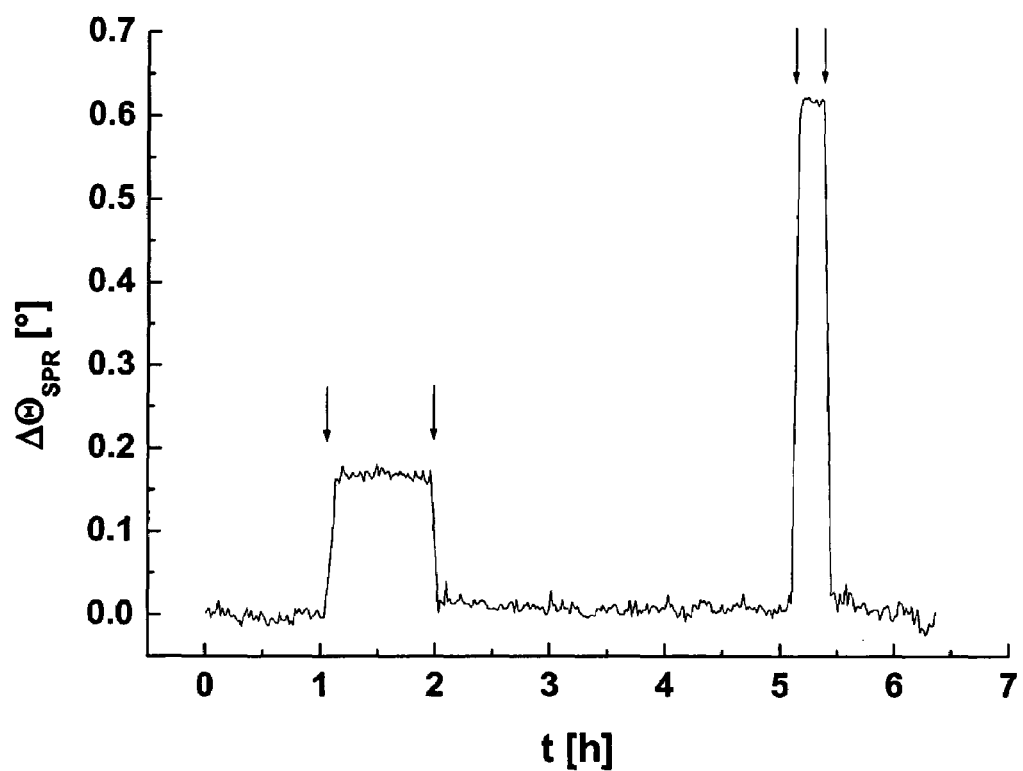
Figure 5:
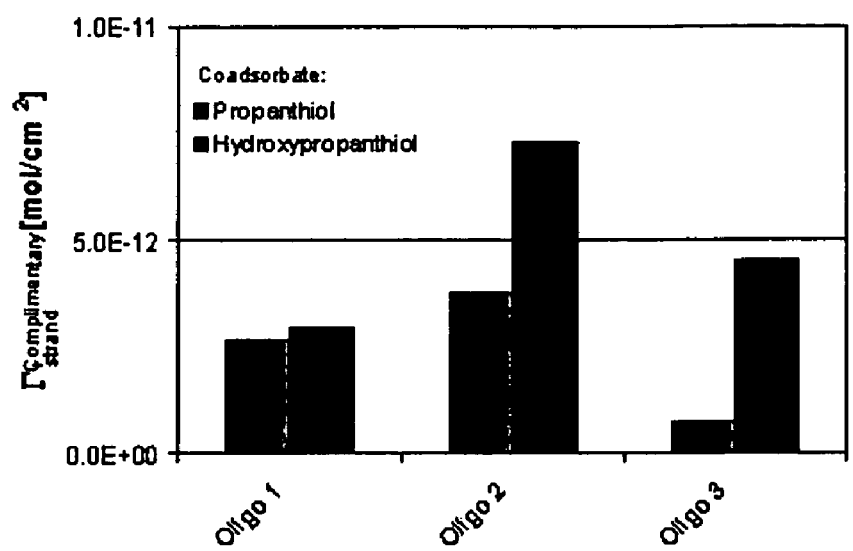
Figure 6:
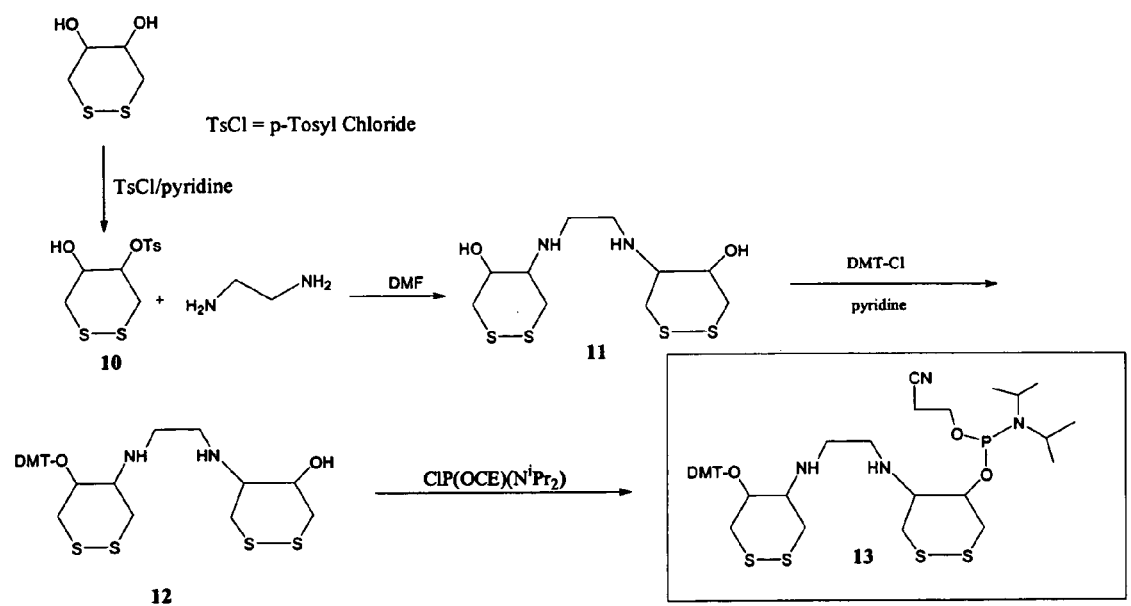
Figure 7:
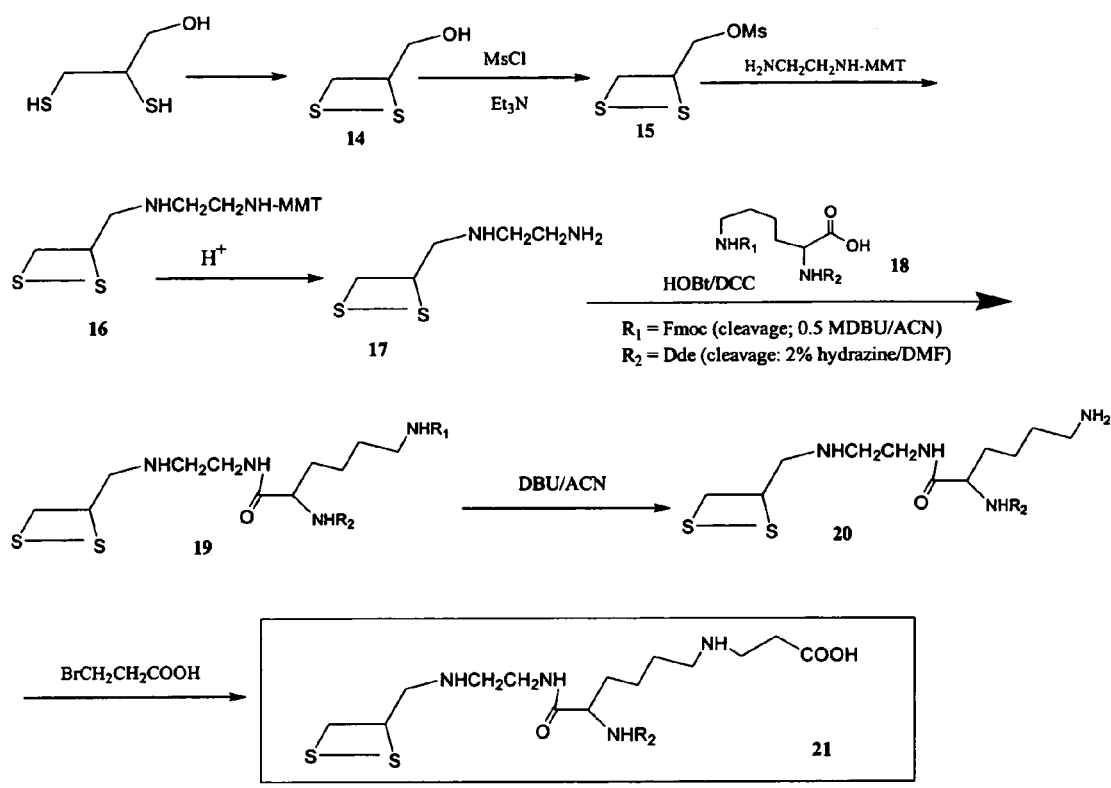
Figure 8:
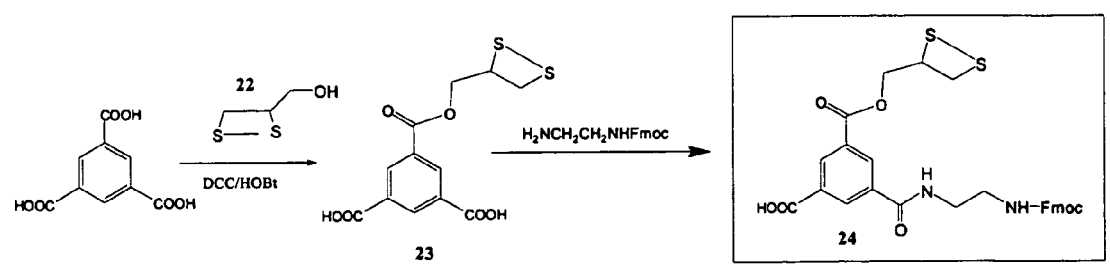
Figure 9:
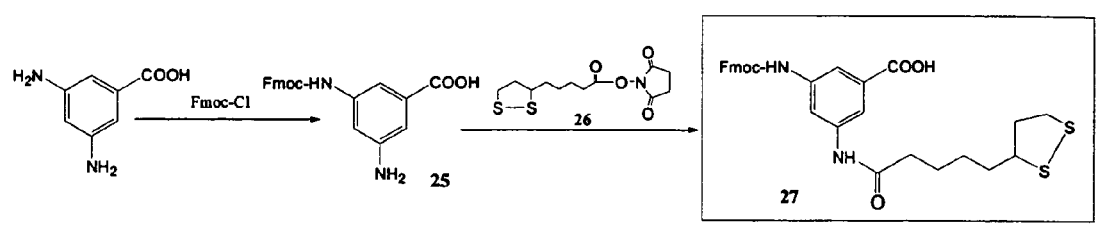

FIG. 1 synthesis scheme according to example 4;

FIG. 2 SPR kinetic for the immobilization of oligonucleotides onto a gold surface according to example 13;

FIG. 3 tests for stability of an oligonucleotide on a gold surface according to example 13;

FIG. 4, FIG. 4.1 and FIG. 4.2 show the results of a square wave voltammetric measurement to prove the hybridizability of the oligonucleotides on a gold surface according to example 13;

FIG. 4.3 and FIG. 4.4 show the results of cyclovoltammetric measurements to quantify the hybridizability of the oligonucleotides on a gold surface according to example 13;

FIG. 5 Shows the extension of the surface coverage by oligonucleotides on a gold surface by integration of the peak areas of the cyclovoltammograms according to example 13;

FIG. 6 synthesis scheme according to example 15;

FIG. 7 synthesis scheme according to example 16;
FIG. 8 synthesis scheme according to example 17;
FIG. 9 synthesis scheme according to example 18.

POSSIBILITIES FOR REALISING THE INVENTION

EXAMPLE 1

Synthesis of 3-O-(4,4'-dimethoxytrityl)-1,4-bis-(4,4'-dimethoxitrityl)-sulfanyl-butan-2-ol

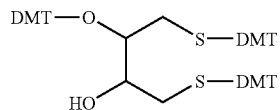

1

In an argon atmosphere 2.0 g (12.9 mmol) of 1,4-Dithiobutan-2,3-diol is dissolved by stirring in 35 ml anhydrous pyridine in a round-bottomed 250 ml flask. 15.3 g (45.15 mmol) of DMT-Cl (4,4'-Dimethoxytrityl Chloride) is added to the clear solution. After 2 hours stirring at room temperature the reaction mixture is heated to 50° C. and is stirred overnight. Thereafter MeOH (2 ml) is added and stirred for 10 min. After concentration in high vacuum the residue is dissolved in 200 ml DCM and is then extracted once with a 1 mol/l NaHCO$_3$ solution and once with a NaCl solution. The organic phase is dried with Na$_2$SO$_4$, filtered and concentrated. For purification of the raw material silica gel 60 is used for chromatography (eluent: ethylacetate/n-heptane/1% Et$_3$N). The product containing fractions are collected and the solvent is evaporated to dryness under vacuum. TLC (silica gel, EtOAc/n-heptane=1:2, +1% Et$_3$N): R$_f$=0.20.

5.90 g (43.2% of the theoretical yield) of a yellowish foaming residue is obtained. $^{13}$C-NMR (CD$_3$Cl) δ (ppm): 33.21 (C-4), 35.82 (C-1), 55.17 (OCH$_3$), 65.50 and 65.82 (C-2 and C-3), 71.52 and 75.02 (S—C$_q$ DMT), 87.03 (O—C$_q$ DMT), 113.01, 126.32, 127.71, 129.30, 131.03, 136.21, 137.13, 145.25, 145.76, 146.10, 157.72, 158.61 (C$_{arom}$ DMT). $^1$H-NMR (CD$_3$Cl) δ (ppm): 2.05-2.21 (m, 4H, CH$_2$-1 und CH$_2$-4), 3.17 (m, 1H, H-3), 3.65 (m, 1H, H-2), 6.72-7.38 (m, 39H$_{arom}$ DMT).

EXAMPLE 2

Synthesis of 3-O-(4,4'-Dimethoxytrityl)-1,4-bis-(4,4'-dimethoxitrityl)-sulfanyl-butan-2-O-(2-cyanoethyl)-N,N'-diisopropylphosphoramidite

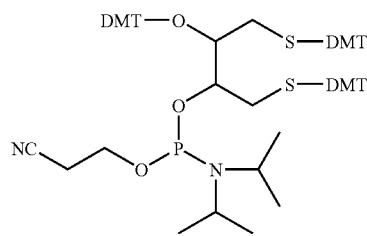

2

In an argon atmosphere 503 mg (0.47 mmol) of 3-O-(4,4'-dimethoxytrityl)-1,4-bis-(4,4'-dimethoxitrityl)sulfanyl-butan-2-ol are dissolved in 4 ml anhydrous ACN. The solution is cooled with ice and 753.2 μl (4.4 mmol) of N,N'-diisopropylethylamine are added dropwise while stirring. 295 μl (1.32 mmol) of chlor-(2-cyanoethoxy)(diisopropylamino)-phosphine are added dropwise using a syringe. After 1.5 hours stirring at room temperature the reaction mixture is diluted with 30 ml DCM and is extracted once with a 1 mol/l NaHCO$_3$ solution and once with a saturated sodium chloride solution. The organic phase is dried with Na$_2$SO$_4$, filtered and concentrated. For purification of the raw material silica gel is used for chromatography (eluent: gradient ethlyacetate/n-heptane 3:1 to 2:1 in the presence of 1% Et$_3$N). Both diastereomeres can be distinguished by TLC as well as by $^{31}$P-NMR: TLC (silica gel, EtOAc/n-heptane=1:2, +1% Et$_3$N): R$_f$(2 diastereomeres)=0.20; 0.27

331.3 mg (55.4% of the theoretical yield) of a white foaming residue is obtained. $^{31}$P-NMR (CD$_3$Cl) δ (ppm): 149.65, 148.59 MS (EI): 303 (DMT$^+$), 1003.1 (M+Na$^+$)

EXAMPLE 3

Synthesis of 5-O-(4,4'-dimethoxytrityl)-(1,2)-dithian-4-ol

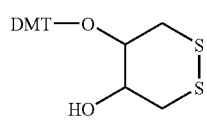

3

A solution of I$_2$ in DCM (9.4 mmol I$_2$ in 120 ml DCM) is added to a solution of 2 g (1.88 mmol) 3-O-(4,4'-dimethoxytrityl)-1,4-bis-(4,4'-dimethoxitrityl)sulfanyl-butan-2-ol and 5 ml pyridine in 100 ml DCM at room temperature. After 10 min of stirring, 200 ml of a 0.5 N Na$_2$S$_2$O$_3$ solution is added. The layers are separated, the organic phase extracted three times with H$_2$O and the combined organic phases dried with Na$_2$SO$_4$. The solvent is evaporated and the remaining foam purified by silica gel chromatography (eluent: gradient of 10-30% EtOAc in n-heptane in presence of 1% Et$_3$N). TLC (silica gel, EtOAc/n-heptane=1:2, +1% Et$_3$N): R$_f$(2 diasteromeres)=0.31; 0.40.

710.7 mg (83.6% of the theoretical yield) of a yellowish oil is obtained. $^{13}$C-NMR (CD$_3$Cl) δ (ppm): 32.76 (C-6), 41.83 (C-3), 55.24 (OCH$_3$), 67.21 (C-5), 72.32 (C-4), 87.25 (C$_q$ DMT), 113.16, 126.64, 127.89, 129.39, 130.61, 136.94, 145.14, 158.09 (C$_{arom}$ DMT). $^1$H-NMR (CD$_3$Cl) δ (ppm): 2.75 (m, 2H, CH$_2$-6), 3.03 (m, 2H, CH$_2$-3), 3.69 (m. 2H, H-4, H-5), 3.79 (s, 3H, OCH$_3$), 6.83-7.52 (m, 13H$_{arom}$ DMT). MS (electrospray ionisation in MeOH): 303 (DMT$^+$), 477 (M+Na$^+$).

EXAMPLE 4

Synthesis of 5-O-(4,4'-dimethoxytrityl)-(1,2)-dithian-4-O-(2-cyanoethyl)-N,N'-diisopropylphosphoramidite

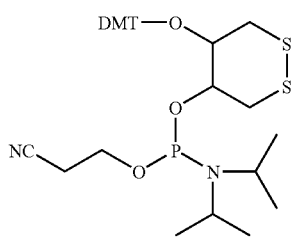

4

A schematic overview of the synthesis is shown in FIG. 1.

In an argon atmosphere 500 mg (1.1 mol) of 5-O-(4,4'-dimethoxytrityl)-(1,2)-dithian-4-ol is dissolved in 8 ml of anhydrous DCM. The solution is cooled with ice and 753.2 µl (4.4 mmol) of N,N'-diisopropylethylamine is added dropwise while stirring. Using a syringe 295 µl (1.32 mmol) of chlor-(2-cyanoethoxy)(diisopropylamino)-phosphine is added dropwise. After 1 hour of stirring at room temperature the reaction mixture is diluted with 50 ml DCM and is extracted once with a 1 mol/l NaHCO$_3$ solution and once with a saturated sodium chloride solution. The organic phase is dried with Na$_2$SO$_4$, filtered and concentrated. For purification of the raw material silica gel chromatography is used (eluent: gradient from 5-15% EtOAc in n-heptane in presence of 1% Et$_3$N). Both diastereomeres can be distinguished by TLC as well as by $^{31}$P-NMR: TLC (silica gel, EtOAc/n-heptane=1:2, +1% Et$_3$N): R$_f$(2 diastereomeres)=0.31; 0.40

459.6 mg (63.8% of the theoretical yield) of the desired product is obtained as a yellowish oil. $^{31}$P-NMR (CD$_3$Cl) δ (ppm): 148.33, 150.19. MS (EI): 303 (DMT$^+$), 655 (M), 677 (M+Na$^+$)

EXAMPLE 5

Synthesis of 1,4-bis-(4,4'-dimethoxitrityl)sulfanyl-butan-2,3-diol

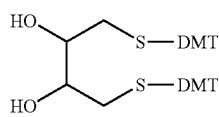

5

In an argon atmosphere 2.2 g (14.3 mmol) of 1,4-dithiobutan-2,3-diol are dissilved by stirring in 40 ml anhydrous pyridine in a round-bottomed 250 ml flask. 9.93 g (29.3 mmol) of DMT-Cl (4,4'-Dimethoxytrityl Chloride) is added to the clear solution. After 2 hours stirring at room temperature 2 ml MeOH is added and the mixture is stirred a further 5 min. The solvent is evaporated, the residue is dissolved in 50 ml DCM and is extracted once with a 1 mol/l NaHCO$_3$ solution and once with a NaCl solution. The organic phase is dried with Na$_2$SO$_4$, filtered and concentrated. The remaining foam is purified by silica gel chromatography (eluent: gradient of 10-30% ethylacetate/n-heptane in presence of 1% Et$_3$N). The product containing fractions are collected and the solvent is evaporated to dryness under vacuum. TLC (silica gel, EtOAc/n-heptane=1:2, +1% Et$_3$N): R$_f$=0.35.

8.66 g (79.8% of the theoretical yield) of a white, foaming residue is obtained. $^{13}$C-NMR (CD$_3$Cl) δ (ppm): 34.83 (C-1, C-4), 55.20 (OCH$_3$ DMT), 65.94 (C-2, C-3), 71.70 (C$_q$ DMT), 113.23, 126.61, 127.95, 129.40, 130.62, 136.96, 145.14, 158.09 (C$_{arom}$ DMT). $^1$H-NMR (CD$_3$Cl) δ (ppm): 2.01 (m, 2H, OH-2, OH-3), 2.35 (m, 4H, C-1, C-4), 3.05 (m, 2H, C-2, C-3), 3.73 (s, 12H, OCH$_3$), 6.78-7.45 (m, 26H$_{arom}$ DMT).

EXAMPLE 6

Synthesis of 3-O-(9-fluorenylmethoxycarbonyl)-1,4-bis-(4,4'-dimethoxitrityl)sulfanyl-butan-2-ol

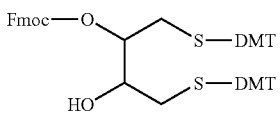

6

In an argon atmosphere 407 mg (1.58 mmol) of 9-Fluorenylmethylchloroformate is added to a solution of 1 g (1.32 mmol) of 1,4-bis-(4,4'-dimethoxitrityl)sulfanyl-butan-2,3-diol in 10 ml anhydrous pyridine. The reaction mixture is stirred overnight at room temperature. Then 500 µl MeOH is added and stirred for 10 min. After concentration of the solvent the residue is dissolved in 30 ml DCM and extracted once with a NaCl solution. After the drying of the organic phase with Na$_2$SO$_4$ and evaporation of the solvent, the raw material is purified by silica gel chromatography (eluent: ethylacetate/n-heptane=3:1). TLC (silica gel, EtOAc/n-heptane=1:2): R$_f$=0.25.

303 mg (23.4% of the theoretical yield) of a white foaming residue is obtained. $^{13}$C-NMR (CD$_3$Cl) δ (ppm): 31.68 (C-4), 35.06 (C-1), 55.20 (OCH$_3$ DMT), 50.36 (CH-Fmoc), 65.31 and 65.45 (C-2 and C-3), 66.77 (CH$_2$-Fmoc), 70.38 (2S-C-DMT), 113.23, 120.05, 124.70, 127.06, 127.6, 128.08, 129.22, 136.24, 136.82, 141.51, 143.31, 144.35, 145.01, 154.36, 158.10, 158.3 (C$_{arom}$ DMT and Fmoc). $^1$H-NMR (CD$_3$Cl) δ (ppm): 2.10-2.45 (m, 4H, CH$_2$-1, CH$_2$-4), 3.73 (d, 12H, OCH$_3$ DMT), 3.98-4.35 (m, 2H, H-3, H-2), 6.78-7.82 (m, 34H, H$_{arom}$ DMT and Fmoc). MS (electrospray ionisation): 303.2 (DMT$^+$), 1283.3 (M+Na$^+$)

EXAMPLE 7

Synthesis of 5-O-(9-fluorenylmethoxycarbonyl)-(1,2)-dithian-4-ol

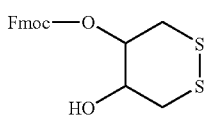

7

A solution of I$_2$ in DCM (6.25 mmol I$_2$ in 60 ml DCM) is added to a solution of 1.23 g (1.25 mmol) 3-O-(9-fluorenylmethyloxycarbonyl)-1,4-S,S'-bis-(4,4'-dimethoxitrity)-butan-2-ol in 50 ml DCM at room temperature. After 10 min 100 ml of 0.5 N Na$_2$S$_2$O$_3$ solution is added during rapid stirring. The layers are separated, the organic phase is extracted three times with H₂O and the combined organic phases are dried with $Na_2SO_4$. The solvent is evaporated and the remaining foam is purified by silica gel chromatography (eluent: gradient of 10-30% EtOAc in n-heptane). TLC (silica gel, EtOAc/n-heptane=1:2): $R_f$=0.20.

212 mg (45.3% of the theoretical yield) of a yellow oil is obtained. $^{13}$C-NMR (CD₃Cl) δ (ppm): 34.51 (C-6), 41.86 (C-3), 46.74 (CH-Fmoc), 65.18 (CH₂-Fmoc), 70.11 (C-5), 72.21 (C-4), 120.06, 125.07, 127.59, 127.98, 141.33, 143.18 ($C_{arom}$ Fmoc) $^1$H-NMR (CD₃Cl) δ (ppm): 2.98 (m, 2H, CH₂-6), 3.09 (m, 2H, CH₂-3), 3.72 (m, 2H, H-4, H-5), 7.28-7.80 (m, 8$H_{arom}$ Fmoc).

EXAMPLE 8

Synthesis of 3-O-(9-fluorenylmethoxycarbonyl)-1,4-bis-(4,4'-dimethoxitrityl)sulfanyl-butan-2-O-(2-cyanoethyl)-N,N'-diisopropylphosphoramidite

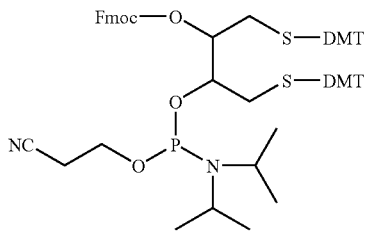

8

In an argon atmosphere 460 mg (0.47 mmol) of 3-O-(9-fluorenylmethoxycarbonyl)-1,4-bis-(4,4'-dimethoxitrityl) sulfanyl-butan-2-ol is dissolved in 5 ml of anhydrous DCM. 322 µl (1.88 mmol) of N,N'-diisopropylethylamine is added to the ice cooled solution dropwise while stirring. 136.5 µl (0.61 mmol) of chlor-(2-cyanoethoxy)(diisopropylamino)-phosphine is added dropwise using a syringe. After 1 hour of stirring at room temperature the reaction mixture is diluted with 50 ml DCM and is extracted once with a 1 mol/l NaHCO₃ solution and once with a saturated sodium chloride solution. The organic phase is dried with $Na_2SO_4$, filtered and concentrated. For purification of the raw material silica gel chromatography is used (eluent: gradient from 5-20% EtOAc in n-heptane in presence of 1% Et₃N). Both diastereomeres can be distinguished by TLC as well as by $^{31}$P-NMR: TLC (silica gel, EtOAc/n-heptane=1:2, +1% Et₃N): $R_f$(2 diastereomeres)=0.26; 0.29

270 mg (48.7% of the theoretical yield) of a white foaming residue is obtained. $^{31}$P-NMR (CD₃Cl) δ (ppm): 149.35, 150.29.

EXAMPLE 9

Synthesis of 5-O-(9-fluorenylmethoxycarbonyl-(1,2)-dithianyl-4-O-(2-cyanoethyl)-N,N'-diisopropylphosphoramidite

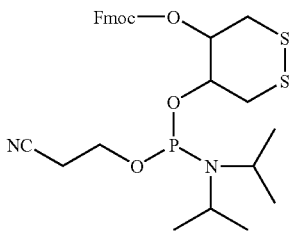

9

In an argon atmosphere 500 mg (1.33 mmol) of 5-O-(9-fluorenylmethoxycarbonyl)-(1,2)-dithianyl-4-ol is dissolved in 5 ml of anhydrous DCM. 914 µl (5.32 mmol) of N,N'-diisopropylethylamine are added dropwise to the ice cooled solution while stirring. 387 µl (1.73 mmol) of chlor-(2-cyanoethoxy)(diisopropylamino)-phosphine is added dropwise using a syringe. After 1.5 hour of stirring at room temperature the reaction mixture is diluted with 50 ml DCM and is extracted once with a 1 mol/l NaHCO₃ solution and once with a saturated sodium chloride solution. The organic phase is dried with $Na_2SO_4$, filtered and concentrated. For purification of the raw material silica gel chromatography is used (eluent: gradient from 5-20% EtOAc in n-heptane in presence of 1% Et₃N). Both diastereomeres can be distinguished by TLC as well as by $^{31}$P-NMR: TLC (silica gel, EtOAc/n-heptane=1:2, +1% Et₃N): $R_f$(2 diastereomeres)=0.22; 0.3

295 mg (48.7% of the theoretical yield) of a white foaming residue is obtained. $^{31}$P-NMR (CD₃Cl) δ (ppm): 149.04, 150.32

EXAMPLE 10

Solid Phase Synthesis of Thiol Modified Oligonucleotides by the Phosphoramidite Method Using the Compound as Described in Example 4

The synthesis of the oligodesoxyribonucleotides was carried out in a 1 µmol synthesis scale using the solid phase phosphoramidite technique with an automated DNA/RNA synthesizer model 384 B (Applied Biosystems) on ®CPG (Controlled Pore Glass), on which the first nucleoside unit was attached by the 3' end. For this the synthesis instrument is for example mounted with reaction columns which are filled with a carrier material preloaded with a nucleobase. In a first reaction step the 5'OH protecting group (4,4'-dimethoxytrityl) is cleaved by treatment with a solution of 2% dichloracetic acid in dichlormethane. After washing the column with acetonitril the coupling of the next building block which can be the modified amidite of example 4 is achieved at the free 5'—OH function by activation with tetrazole in acetonitril. For incorporation of the modified amidite respectively a 10 min double coupling step is used. The existing still trivalent P atom is transferred after renewed washing into the natural pentavalent phosphate by oxidation with a solution of Iodine in THF/Lutidin/H₂O. The following capping step by acetic anhydride/1-methylimidazole blocks free 5'—OH groups by acetylation. Thus the building of failure sequences are suppressed. After washing the synthesis cycle starts over again with renewed cleavage of the 5'-O-dimethoxytrityl protecting group. In this way the modified oligonucleotide is built up. The last DMT group was not cleaved. After completed synthesis the oligonucleotide bound to the carrier was set free by treatment with concentrated ammoniac solution in water. The protecting groups at the heterocycles were removed in the same solution within 16 h at 37° C. The samples were concentrated to approx. 200 µl in vacuum and purified by HPLC.

EXAMPLE 11

Solid Phase Synthesis of Thiol Modified Oligonucleotides by the Phosphoramidite Method Using the Compound as Described in Example 9

The oligomer synthesis takes place as described in example 10. For the deprotection of the Fmoc group the oligonucleotide at the carrier is treated with a solution of 0.5 mol/l DBU in acetonitril (4×1 ml 0.5 mol/l DBU/ACN in 2 min). The work up procedure also follows that in example 10.

EXAMPLE 12

Solid Phase Synthesis of Thiol Modified Oligonucleotides by the Phosphoramidite Method Using the Compound as Described in Example 2

The oxidation step is carried out using a 0.1 mol/l iodine solution with extended reaction times (1 min). The further synthesis cycle and the work up procedure of the oligonucleotides is as described in example 10.

EXAMPLE 13

HPLC Purificaton of Trityl Protected Oligonucleotides

In the first purification step the DMT protected oligomers are purified by HPLC with a RP-C18 silica gel column (eluent: 0.1 mol/l triethylammoniumacetate buffer, acetonitril). The oligomers were treated with 100 µl of an 80% acetic acid solution and shaken for 20 min at room temperature. 100 µl $H_2O$ und 60 µl 3 mol/l NaAc solution was added to that solution. The oligonucleotides were treated with 1.5 ml EtOH and completely precipitated at −20° C. (20 min). After centrifugation and decanting of the ethanol, the pellet is dried in vacuum. The characterisation of the oligomers was effected using MALDI-TOF MS. Table 1 shows the retention times of the synthesized oligonucleotides.

TABLE 1

| oligomer (5'->3'-direction) (sequence) | retention times (min) with DMT |
|---|---|
| oligonucleotide 1: 5'-XAGG TGA CTG TGT TAT CCG CA-3' | 10.05 |
| oligonucleotide 2: 5'-XXAGG TGA CTG TGT TAT CCG CA-3' | 11.30 |
| oligonucleotide 3: 5'-XXXAGG TGA CTG TGT TAT CCG CA-3' where X is compound 4 | 11.72 |
| 5'-XT10-3' | 21.12 |
| 5'-XXT10-3' where X is compound 2 | 21.52 |

EXAMPLE 14

Experiments for Immobilization of Oligonucleotides 1, 2 and 3 According to Example 13

Preparation of Single-strand DNA Monolayer
a) Cleaning of Au Electrodes
To remove impurities on the gold surface the gold covered glas slides were immersed in a mixture (3:1) of concentrated sulfuric acid and hydrogen peroxide solution (30%) for 30 seconds. The electrodes were rinsed thoroughly with deionized water and placed in pure ethanol for 15 minutes.

b) Immobilization of Oligonucleotides 1, 2 and 3 on Gold Surfaces

Oligonucleotides were immobilized on gold surfaces overnight by self assembly from 30 µM solutions in 500 mM potassium phosphate buffer (pH 7.0). After adsorption the electrodes were rinsed thoroughly with potassium phosphate buffer.

Surface Plasmon Resonance spectroscopy (SPR) was used to examine the effectiveness of immobilization. SPR is highly sensitive to changes of refractive index at the metal interface that are a byproduct of adsorption and desorption processes. The shifting $\Delta\Theta$ of the resonance angle is directly proportional to mass increase or decrease at the surface. Experiments were carried out with a Biosuplar II (from Analytical µ-Systems, Regensburg, Germany).

FIG. 2 illustrates the SPR kinetics of the immobilization of oligonucleotides oligo 1 (■), oligo 2 (▲) and oligo 3 (●) onto a gold surface (c=30 µM in 500 mM potassium phosphate buffer, pH 7). It can be seen from the plot that oligonucleotides 1, 2 and 3 show roughly identical kinetic behaviour for the immobilization process. The amount adsorbed on the surface is less than that of comparable oligonucleotides with a single thiol anchor (□) ($H_2N$—$C_6$-TCG TCA CTG TCA GTG TCA GA-[$C_3$—S—S—$C_3$—OH] with $C_3$=$(CH_2)_3$ and $C_6$=$(CH_2)_6$), which reflects the higher spacial requirement per DNA strand.

c) Coadsorption of Alkane Thiols

The oligonucleotide-modified gold surface was treated with short-chain alkane thiols in order to put the DNA in a more upright position and to passivate gaps on the surface. This coadsorption was carried out for 30 minutes with a 1 mM solution of the corresponding thiol (propane thiol or 3-hydroxy propane thiol) in the above-mentioned potassium phosphate buffer containing 1% ethanol followed by a thorough rinsing with potassium phosphate buffer.

Stability Tests:

The stability of immobilization was checked by incubating the surfaces with phosphate buffer (pH 9) and applying conditions for dehybridization (2 mol/l NaOH) under SPR control. FIG. 3 illustrates a stability test for a monolayer of oligonucleotide 1 coadsorbed with propanethiol. At the point in time t=0 the oligonucleotide monolayer coadsorbed with propanethiol is subjected to 500 mM phosphate buffer at pH 7. At t=1 h the buffer was replaced with 500 mM phosphate buffer at pH 9. The resonance angle is shifted as a result of the higher refractive index of this buffer. Subsequently at t=2 h, the buffer was changed back to the original 500 mol/l phosphate buffer at pH 7 with the resonance angle also returning to its initial value. The amount of substance on the surface did not change during the treatment with buffer at pH 9. At t=5 h the buffer was replaced by 2 mol/l NaOH and finally at t=5.5 h again changed back to phosphate buffer, pH 7. Also when subjected to these conditions, the monolayer remains stable without any loss of material.

Verification of Hybridizability

In order to check the hybridizability, the above oligonucleotide monolayer was hybridized with a complementary strand double-labeled with ferrocenyl acetic acid ([FcAc—Y]$_2$—C GGA TAA CAC AGT CAC CT; Y=Amino Introducing Reagent with C3-spacer; Chemgene). The hybridization was performed by incubation of the monolayer with a 100 mmol/l sodium sulfate solution containing 1 µmol/l of complementary strand heated to 95° C., followed by cooling down over a period of at least 2 hours.

Square Wave and Cyclic voltammetric methods were employed for electrochemical characterization. Both methods can be used for the detection of surface-bound redox label (here ferrocenyl acetic acid).

With square wave voltammetry a linear voltage ramp is superimposed on a square wave potential at a frequency f and an amplitude $E^~$ (in the example f=10 Hz, $E^~$=20 mV rms) and the current is detected at the end of every pulse. Through this the capacitive charging current is virtually eliminated, resulting in a voltammetric peak. A relative comparison is easily done, whereas absolute quantification is unproblematic.

With cyclic voltammetry a triangular voltage wave is driven and the resulting current is detected. Distinctive capacitive charging currents can complicate the quantification of faradayic currents. However, the number of transferred charges and thus the number of redox labels can be determined by the integration of peak areas.

Using the square wave voltammetry described above it was checked whether the redox label of the hybridized complementary strand could be detected. The figures 4.1 and 4.2 illustrate the square wave voltammogram (f=10 Hz, $E^\sim$=20 mV rms) for the oligonucleotide monolayer 1-3 coadsorbed with propanethiol (4.1) and hydroyx-propanethiol (4.2) and hybridized with the redox labeled complementary strand. All monolayers show a distinct peak at +0.23 V (vs Ag/AgCl/3M KCl), which is caused by oxidation of the ferrocenyl acetic acid on the complementary strand and indicates a successful hybridization of the monolayer. However the peak currents and consequently the hybridization efficiency varies depending on the coadsorption and oligonucleotide applied.

Cyclic voltammetry was used for quantification. By integration of the cyclic voltammograms (v=500 mV/s) in FIGS. 4.3 and 4.4 the number of redox labels and thus the surface concentration $\Gamma$ of the complementary strand (roughness factor=2, number of labels per target=2) is determined and plotted in FIG. 5. The surface concentration $\Gamma$ is in direct proportion to the hybrizability of the oligonucleotide monolayer.

Among the three oligonucleotides in example 13, oligonucleotide 2 shows the best hybridizability. The hybridizability of the ssDNA monolayer coadsorbed with hydroxypropanethiol is thus significantly higher as compared with the respective monolayer coadsorbed with propanethiol. The surface coverage is between $1 \cdot 10^{-12} - 7 \cdot 10^{12}$ mol/cm$^2$ and is thus in a range that has already been determined by other groups (Herne T. M., Tarlov M. J. *J. Am. Chem. Soc.* 1997, 119, 8916-8920).

All the above electrochemical experiments were carried out in a three-electrode setup with the gold working electrode to be analyzed, a Pt counter electrode and a reference electrode (Ag/AgCl/3M KCl) using an Autolab 12 potentiostat (Ecochemie, Netherlands).

EXAMPLE 15

2 mmol of p-tosyl chloride is added to a solution of trans-1,2-dithiane-4,5-diol (2 mmol in anhydrous pyridine). After stirring for 2 hours at room temperature the solvent is evaporated. 0.5 eq ethylene diamine in DMF is stirred in the presence of NaH for 10 min at room temperature. Compound 10 (see FIG. 6) is dissolved in DMF and added to the ethylendiamin solution above. The reaction mixture is stirred under reflux for 6 hours. The desired product 11 (see FIG. 6) is isolated by silica gel chromatography and reacted with 1 eq DMT-Cl in pyridine obtaining product 12 (see FIG. 6). The DMT protected product is purified by silica gel chromatography (eluent: ethylacetate/n-heptane in presence of 1% Et$_3$N). 1 mmol of product 12 (see FIG. 6) is dissolved in 10 ml of anhydrous DCM in an argon atmosphere. The solution is cooled in an ice bath and 4 eq of N,N'-diisopropylethylamine is added dropwise while stirring. Using a syringe, 1.2 eq of chlor-(2-cyanoethoxy)(diisopropylamino)-phosphine is added dropwise. After 1.5 hours of stirring at room temperature the reaction mixture is diluted with DCM and worked up with standard methods. For purification of product 13 (see FIG. 6) silica gel chromatography is used (eluent: ethylacetate/n-heptane in presence of 1% Et$_3$N).

EXAMPLE 16

1 g (8 mmol) of 2,3-dimercapto-1-propanol is dissolved in ACN and oxidized by air (oxygen). The corresponding cyclic compound 14 (see FIG. 7) is reacted with MsCl (Mesylchloride) in the presence of Et$_3$N. After 2 hours stirring at room temperature the solvent is evaporated in a rotary evaporator. A solution of 1 eq MMT-Ethylendiamine is treated with NaH in DMF. After 30 min stirring at room temperature 1 eq of compound 14 (see FIG. 7) in DMF is added to the MMT-Ethylendiamine solution above. The reaction mixture is stirred under reflux for 4 hours. The solvent is reduced with a rotary evaporator, the residue is worked up with standard methods and purified with silica gel chromatography.

The MMT group of compound 16 (see FIG. 7) is cleaved with an acidic solution (2% DCA in DMF). 1 eq of compound 17 (see FIG. 7) is dissolved in DMF and reacted with N-α-Fmoc-N-ε-1-(4,4-dimethyl-2,6-dioxocyclohex-1-ylidene) ethyl-L-Lysine (compound 18 (see FIG. 7)) in presence of HOBt and DCC. The reaction is carried out overnight at room temperature. The solvent is evaporated and the residue is worked up with standard methods and purified with silica gel chromatography using ethylacetate/n-heptane as eluent.

The FMOC group of compound 19 (see FIG. 7) is cleaved selectively with a solution of 500 mmol/l DBU in ACN. The free amino group of product 20 (see FIG. 7) reacts with BrCH$_2$CH$_2$COOH to obtain product 21 (see FIG. 7) as the main product. The raw material is purified with silica gel chromatography using ethylacetate/n-heptane as eluent.

EXAMPLE 17

1 eq each of compund 22 (see FIG. 8), DCC and HOBt is added to a solution of 1 g (4.7 mmol) of 1,3,5-Benzenetricarboxylic acid in anhydrous DMF. The reaction mixture is stirred overnight at room temperature. The solvent is concentrated and the desired product 23 (see FIG. 8) is isolated with silica gel chromatography. Compound 23 (see FIG. 8) is dissolved in DMF and reacts with Fmoc-ethylendiamine in the presence of DCC and HOBt. After reducing the solvent in a vacuum, the raw product is purified with silica gel chromatography using ethylacetate/n-heptane as eluent.

EXAMPLE 18

1.2 eq of Fmoc-Cl ((9-Fluorenylmethyl)-chloroformate) are added to a solution of 2 g (13 mmol) of 3,5-Diamino benzoic acid in 40 ml anhydrous pyridine. After 2 hours stirring at room temperature the solvent is evaporated and the raw product is purified with silica gel chromatography using ethylacetate/n-heptane as eluent. Compound 25 (see FIG. 9) is dissolved in a mixture of ACN and dioxane and reacted with lipoic acid N-Hydroxy-succinimide ester. The reaction mixture is stirred overnight at room temperature. The solvent is removed with a rotary evaporator and the residue is dissloved in DCM and worked up with standard methods. The raw product is purified with silica gel chromatography using ethylacetate/n-heptane as eluent to isolate the desired product 27 (see FIG. 9).

The invention claimed is:

1. 3,4-disubstituted-1,2-dithiocyclohexane compounds of the formula

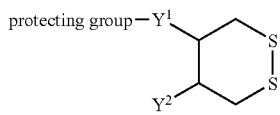

wherein protecting-group-$Y^1$ is protecting-group-NH, protecting-group-$NR^4$, protecting-group-O, CONH-protecting-group, protecting-group-OOC, protecting-group-S—S, —CH(protecting-group-O)$_2$, or protecting-group-S, wherein protecting-group is chosen from the group consisting of triphenylmethyl-, t-butoxycarbonyl-, benzyl-, 2,4-dinitrophenyl-, 9-fluorenylmethoxycarbonyl-, allyloxycarbonyl-, benzyloxymethyl-, 4-azidobenzyloxycarbonyl-, acetamidomethyl-, 1-adamantyl-, 1-adamantyloxycarbonyl-, anisyl, benzamidomethyl-, biphenyldimethylsilyl-, 2,4-dimethylthiophenoxycarbonyl-, 1-methyl-1-(4-biphenyl)ethoxycarbonyl-, benzothiazole-2-sulfonyl-, t-butoxymethyl-, benzoyl-, benzyloxycarbonyl-, cyclohexan-1,2-diacetal-, cyclohexyl-, 2-(4,4-dimethyl-2,6-dioxocyclohexylidene)ethyl-, 1-methyl-1-(3,5-dimethoxyphenyl)ethoxycarbonyl-, diethylisopropylsilyl-, 1,3-dithianyl-2-methyl-, 2,4-dimethoxybenzyl-, dithianylmethoxycarbonyl-, dimethoxytrityl-, p,p'-dinitrobenzhydryl-, 2,4-dinitrophenyl-, 2,4-dimethylpent-3-yloxycarbonyl-, 2-(diphenylphosphino)ethyl-, 9-fluorenylmethyl-, levulinoyl-, p-methoxybenzensulfonyl-, 2,6-dimethoxy-4-methoxybenzensulfonyl-, monomethoxytrityl-, methoxyphenylsulfonyl-, mesitylensulfonyl-, o-nitrobenzyl-, 2-[2-(benzyloxy)ethyl]benzoyl-, 3-(3-pyridyl)allyloxycarbonyl-, 2,2,5,7,8-pentamethylchroman-6-sulfonyl-, pivaloyloxymethyl-, t-butyldimethylsilyl-, t-butyldiphenylsilyl-, 2,2,2-trichloro-1,1-dimethylethyl-, trifluoroacetyl-, triisobutylsilyl-, 2,4,6-trimethylbenzyl-, trimethoxybenzyl-, p-toluensulfonyl- or benzyloxycarbonyl-, $Y^2$ is —OH, —NH$_2$, —NHR$^3$, —NR$^3$R$^4$, —COOH, —COCl, —COOCO—R$^6$, —CONH$_2$, —CONHR$^3$, —COOR$^3$, —SO$_3$H, —SO$_3$Cl, —SH, —S—SR$^3$, —CHO, —COR$^3$, —C$_2$H$_3$O, halogen, —N$_3$, —NH—NH$_2$, —NCO, —NCS, wherein R$^3$ is alkyl, heteroalkyl, aryl, cycloalkyl or a protecting group, wherein R$^3$ in the groups Y$^1$ and Y$^2$ may be equal or different, R$^4$ is a protecting group, wherein R$^4$ in the groups Y$^1$ and Y$^2$ may be equal or different, and wherein R$^4$ and R$^3$ may be equal or different, R$^6$ is alkyl, heteroalkyl, aryl, or cycloalkyl, wherein R$^6$ in the groups Y$^1$ and Y$^2$ may be equal or different, wherein Y$^2$ may also be a group of the formula (II) or (III),

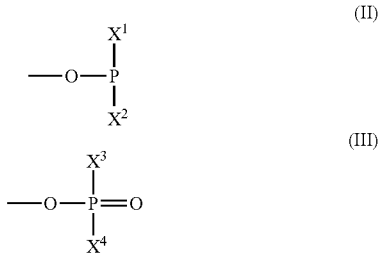

wherein

X$^1$ is halogen or substituted amine,

X$^2$ is alkyl, alkoxy, aryloxy or a cyano derivative of alkyl, alkoxy, aryloxy, X$^3$ is halogen, amino group or oxygen and X$^4$ is alkyl, alkoxy, aryloxy or X$^4$ is H if X$^3$ is oxygen.

2. The compounds according to claim 1 wherein protecting-group-Y$^1$ is protecting-group-OOC, protecting-group-O, protecting-group-S, protecting-group-NH or protecting-group-NR$^y$ and Y$^2$ is COOH, COOR$^x$, OH, OR$^x$, SH, SR$^x$, NH$_2$, NHR$^x$, NR$^x$R$^y$, wherein R$^x$ is a protecting group and R$^y$ is alkyl having no more than 15 C atoms, aryl having no more than 14 C atoms, cycloalkyl having no more than 15 C atoms, heteroalkyl having no more than 15 C atoms, a protecting group or a group of the formula (II) or (III).

* * * * *